(12) United States Patent
Wang et al.

(10) Patent No.: US 10,787,635 B2
(45) Date of Patent: Sep. 29, 2020

(54) METHOD AND KIT FOR EXPANDING CIRCULATING TUMOR CELLS IN VITRO

(71) Applicant: Taipei Medical University, Taipei (TW)

(72) Inventors: Peng-Yuan Wang, Taipei (TW); Yin-Ju Chen, Taipei (TW); Long-Sheng Lu, Taipei (TW); Thierry Burnouf, Taipei (TW)

(73) Assignee: Taipei Medical University, Taipei (TW)

( * ) Notice: Subject to any disclaimer, the term of this patent is extended or adjusted under 35 U.S.C. 154(b) by 310 days.

(21) Appl. No.: 16/029,680

(22) Filed: Jul. 9, 2018

(65) Prior Publication Data
US 2019/0300832 A1   Oct. 3, 2019

(30) Foreign Application Priority Data
Mar. 29, 2018   (TW) .............................. 107111077 A

(51) Int. Cl.
C12M 1/12     (2006.01)
C12N 5/09     (2010.01)
G01N 33/50    (2006.01)

(52) U.S. Cl.
CPC ........... C12M 25/18 (2013.01); C12N 5/0693 (2013.01); G01N 33/5011 (2013.01); *C12N 2500/84* (2013.01); *C12N 2535/00* (2013.01)

(58) Field of Classification Search
CPC . C12M 25/18; G01N 33/5011; C12N 5/0693; C12N 2535/00; C12N 2500/84
See application file for complete search history.

(56) References Cited

U.S. PATENT DOCUMENTS 8,669,044 B2     3/2014   Chiu et al.
2008/0248499 A1*  10/2008  Chiu ................. B01L 3/502746
                                                           435/7.23

FOREIGN PATENT DOCUMENTS

CN    103154740 A    6/2013

OTHER PUBLICATIONS

Zheng et al., Aptamer-functionalized barcode particles for the capture and detection of multiple types of circulating tumor cells. Advanced Materials, vol. 26, No. 43 (Nov. 18, 2014) pp. 7333-7338. (Year: 2014).*
Yu et al., Ex vivo culture of circulating breast tumor cells for indivualized testing of drug susceptibility. Science, vol. 345, No. 6193 (Jul. 11, 2014) pp. 216-220. (Year: 2014).*
Sheng et al., Capture, release and culture of circulating tumor cells from pancreatic cancer patients using an enhanced mixing chip. Royal Society of Chemistry, vol. 14 (2014) pp. 89-98. (Year: 2014).*
Zheng, Fuyin, et. al., "Aptamer-Functionalized Barcode Particles for the Capture and Detection of Multiple Types of Circulation Tumor Cells.", Advanced materials 26. 43(2014), pp. 7333-7338.
Office Action issued in corresponding Taiwan patent application No. 107111077 dated Apr. 30, 2019.

* cited by examiner

*Primary Examiner* — Kara D Johnson
(74) *Attorney, Agent, or Firm* — Idea Intellectual Limited; Margaret A. Burke; Sam T. Yip

(57) ABSTRACT

A method for expanding circulating tumor cell in vitro includes preparing a cell culture tool having a multi-particle colloidal crystal layer, preparing a cell solution including circulating tumor cells, and contacting the cell solution with the multi-particle colloidal crystal layer, to attach the circulating tumor cells in the cell solution to the multi-particle colloidal crystal layer and rapidly expand by 20 times or more. The multi-particle colloidal crystal layer at least includes first particles having a particle size of 1000 to 5000 nm and second particles having a particle size of 20 to 400 nm. The culture medium in the cell solution at least includes a platelet lysate.

10 Claims, 28 Drawing Sheets

(12 of 28 Drawing Sheet(s) Filed in Color)

US 10,787,635 B2

METHOD AND KIT FOR EXPANDING CIRCULATING TUMOR CELLS IN VITRO

CROSS-REFERENCE TO RELATED APPLICATION

This non-provisional application claims priority under 35 U.S.C. § 119(a) to Patent Application No. 107111077 filed in Taiwan, R.O.C. on Mar. 29, 2018, the entire contents of which are hereby incorporated by reference.

BACKGROUND

Technical Field

The present invention relates to a cell culture technology, and particularly to a method and kit for expanding circulating tumor cells in vitro.

Related Art

At present, for the use of anti-cancer drugs, the clinicians rely mainly on statistical analysis of clinical treatments to determine the choice of anti-cancer drugs and plan the course of treatment for the patients with cancers. In these processes, the patient's response to the drug can be evaluated only after a period of time after the course of treatment is completed. Moreover, when a drug or a changed medical prescription is given to the patients, it is not possible to determine an appropriate drug based on individual differences of the patients. Therefore, in order to improve the success rate of cancer treatment, detection according to the specific nature of cancers among individuals and constant evaluation of the response to the drugs during the course of treatment can provide a clinically tailored therapeutic approach.

When cancer cells are detached from the primary tumor and enter into the blood vessels, the cancer cells in the blood are called circulating tumor cells (CTCs). CTC count is a new approach of cancer biomarker. Many studies have confirmed that this approach can be used to predict the prognosis of cancers and monitor the response of cells to chemotherapy and targeted therapy. Currently, in many CTC-related clinical applications, the development of diseases is generally determined based on CTC count. However, although it has been confirmed theoretically in several research papers that CTC can immediately and directly reflect the patient's response to drugs, this approach still cannot be used widely. Due to the limitation by the lack of suitable technology to expand the number of CTCs, accurate genetic testing cannot be achieved with a small number of CTCs and no sufficient number of CTCs are available for drug test. Moreover, the CTC culture in vitro is quite low in success rate (less than 20%) and is time consuming (over six months or more).

SUMMARY

In an embodiment, a method for expanding circulating tumor cells in vitro comprises preparing a cell culture tool having a multi-particle colloidal crystal layer, preparing a cell solution, and contacting the cell solution with the multi-particle colloidal crystal layer, to attach the circulating tumor cells to the multi-particle colloidal crystal layer and expand to a given condition. The cell culture tool comprises a two-dimensional planar surface and the multi-particle colloidal crystal layer located on the two-dimensional planar surface. Moreover, the multi-particle colloidal crystal layer comprises first particles having a particle size of 1000 to 5000 nm and second particles having a particle size of 20 to 400 nm. The cell solution comprises a culture medium and the circulating tumor cells. Furthermore, the culture medium comprises a platelet lysate.

In an embodiment, a kit for expanding circulating tumor cells in vitro comprises culture medium materials and a cell culture tool. The culture medium materials are used to formulate a culture medium comprising a platelet lysate. The cell culture tool is used to hold the culture medium and comprises a two-dimensional planar surface and a multi-particle colloidal crystal layer located on the two-dimensional planar surface. The multi-particle colloidal crystal layer comprises first particles having a particle size of 1000 to 5000 nm and second particles having a particle size of 20 to 400 nm.

In summary, according to the method and kit for expanding circulating tumor cells in vitro provided in the embodiments of the present invention, a cell culture tool having a multi-particle colloidal crystal layer with a suitable range of particle sizes formed on a surface thereof is used, to attach the circulating tumor cells thereon and expand efficiently, and the expanded circulating tumor cells can be used for drug evaluation.

BRIEF DESCRIPTION OF THE DRAWINGS

The patent of application file contains at least one drawing executed in color. Copies of this patent or patent application publication with color drawing(s) will be provided by the office upon request and payment of the necessary fee.

The present invention will become more fully understood from the detailed description given herein below for illustration only, and thus are not limitative of the present invention, and wherein.

DETAILED DESCRIPTION

Figure 1:
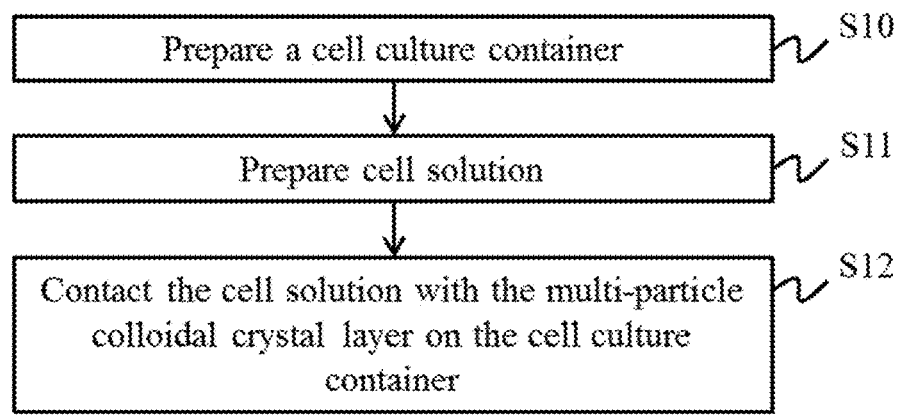
FIG. 1 is a flow chart of a method for expanding circulating tumor cells in vitro according to an embodiment of the present invention.
Figure 2:
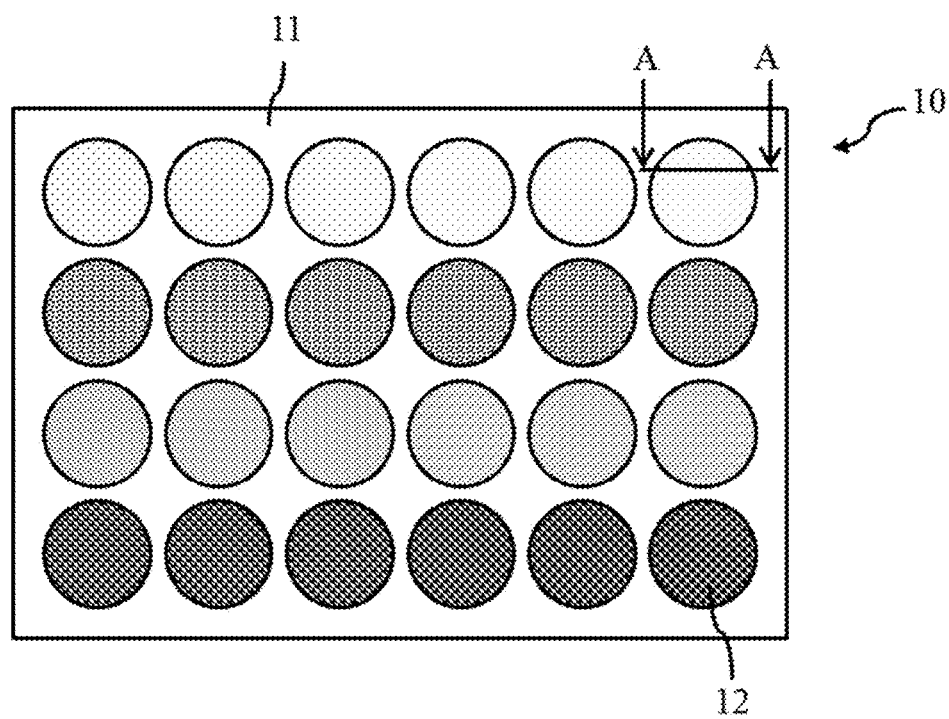
FIG. 2 is a top view of a cell culture tool according to an embodiment of the present invention.
Figure 3:
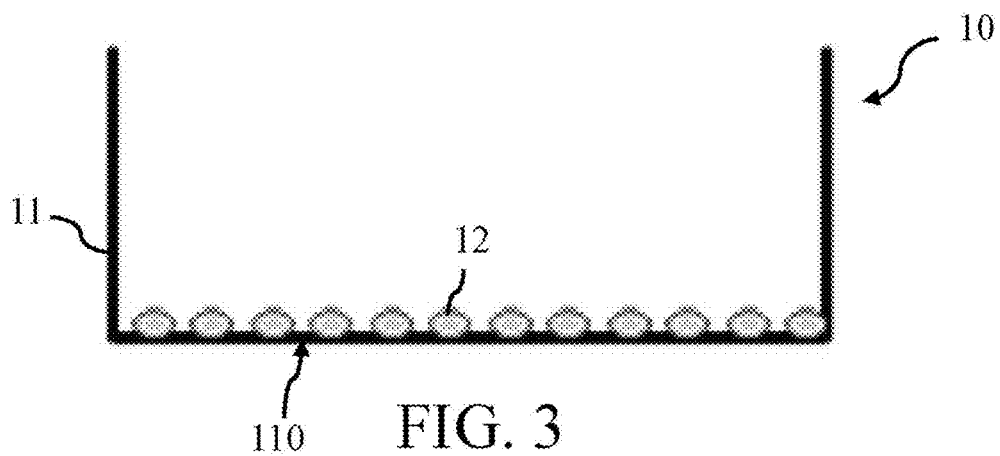
FIG. 3 is a schematic cross-sectional view of the cell culture tool shown in FIG. 2 alone line AA.

Referring to FIGS. 1 to 3, in some embodiments, a method for expanding circulating tumor cells in vitro comprises the following steps. Firstly, a cell culture tool 10 for holding a cell solution is prepared (Step S10). In some embodiments, the cell culture tool 10 comprises a substrate 11 and a multi-particle colloidal crystal layer 12. The substrate 11 has a two-dimensional planar surface 110. The multi-particle colloidal crystal layer 12 is located on the two-dimensional planar surface 110 of the substrate 11. The cell culture tool 10 may be a culture dish, a culture plate, a glass slide, a plastic slide, and so on. In other words, the substrate 11 may be a common culture dish, a common culture plate, a glass slide or a plastic slide. For example, the substrate 11 of the cell culture tool 10 may include, but is not limited to, for example, a multi-well plate having at least 6 wells or a multi-well plate having up to 96 wells.

Then, a cell solution 20 is prepared (Step S11). Here, the cell solution 20 comprises circulating tumor cells 21 and a culture medium 22 containing a platelet lysate. In an embodiment, the circulating tumor cells 21 may be isolated from the blood of a living organism first, and then the isolated circulating tumor cells 21 are mixed with the culture medium 22 to form the cell solution 20. In another embodiment, the blood containing the circulating tumor cells 21 is directly mixed with the culture medium 22 to form the cell solution 20 without screening the circulating tumor cells 21 first.

Figure 4:
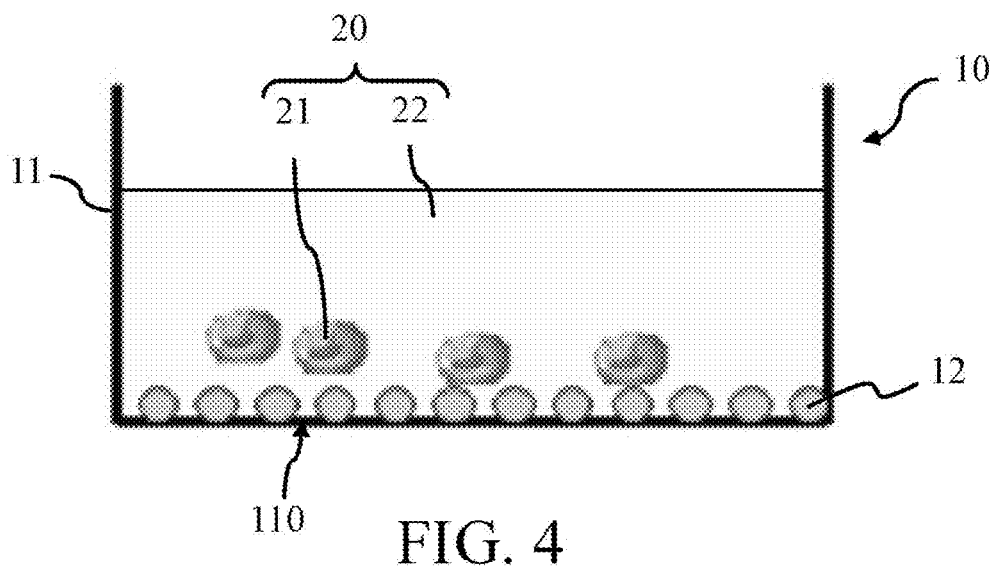
FIG. 4 schematically shows an implementation state of the cell culture tool as shown in FIG. 3 after the cell solution is added.
Figure 5:
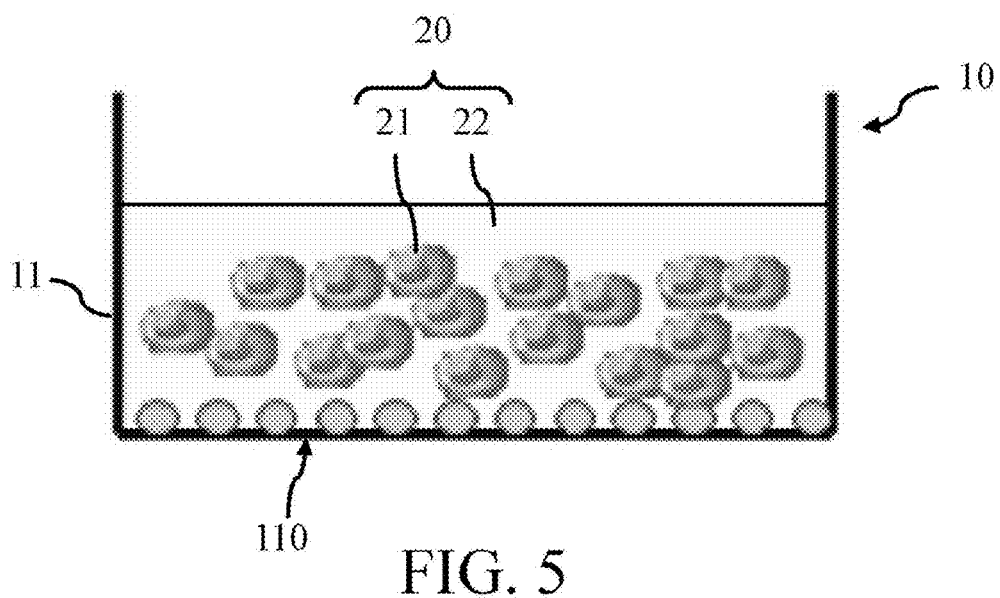
FIG. 5 schematically shows the states of the cell culture tool and the cell solution as shown in FIG. 4 after culturing.
Figure 6:
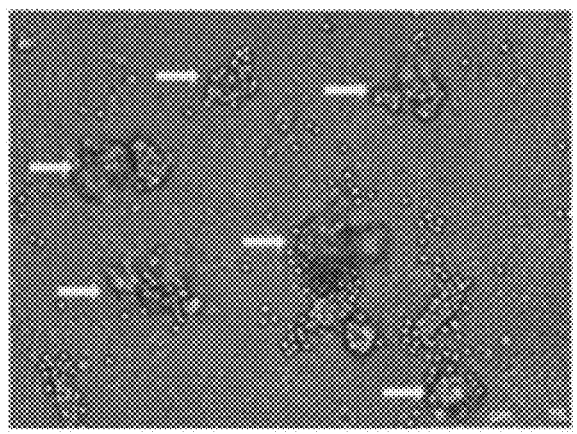
FIG. 6 is an optical micrograph showing the surface of a multi-particle colloidal crystal layer having colonies of circulating tumor cells formed thereon through the method for expanding circulating tumor cells in vitro according to an embodiment of the present invention.

Then, the cell solution 20 is contacted with the multi-particle colloidal crystal layer 12 on the cell culture tool 10 (as shown in FIG. 4) (Step S12), to attach the circulating tumor cells 21 in the cell solution 20 to the multi-particle colloidal crystal layer 21 and expand to a given condition (as shown in FIG. 5). In some embodiments, the given condition may be that the circulating tumor cells 21 attached to the multi-particle colloidal crystal layer 12 are expanded to have a cell density that is over 20 times the initial cell density inoculated in a short time (6 weeks or less). For example, in three to four weeks, the circulating tumor cells 21 attached to the multi-particle colloidal crystal layer 12 are expanded by 20 times or more. For example, after Step S12, the surface of the multi-particle colloidal crystal layer 12 is observed under an optical microscope, and colonies formed by the circulating tumor cells 21 after amplification on the multi-particle colloidal crystal layer are observed (indicated by the arrows), as shown in FIG. 6.

In some embodiments, the multi-particle colloidal crystal layer 12 comprises two kinds of particles (referred to as first particles and second particles hereinafter). The first particles have a particle size of 1000 to 5000 nm, and the second particles have a particle size of 20 to 400 nm.

Figure 7:
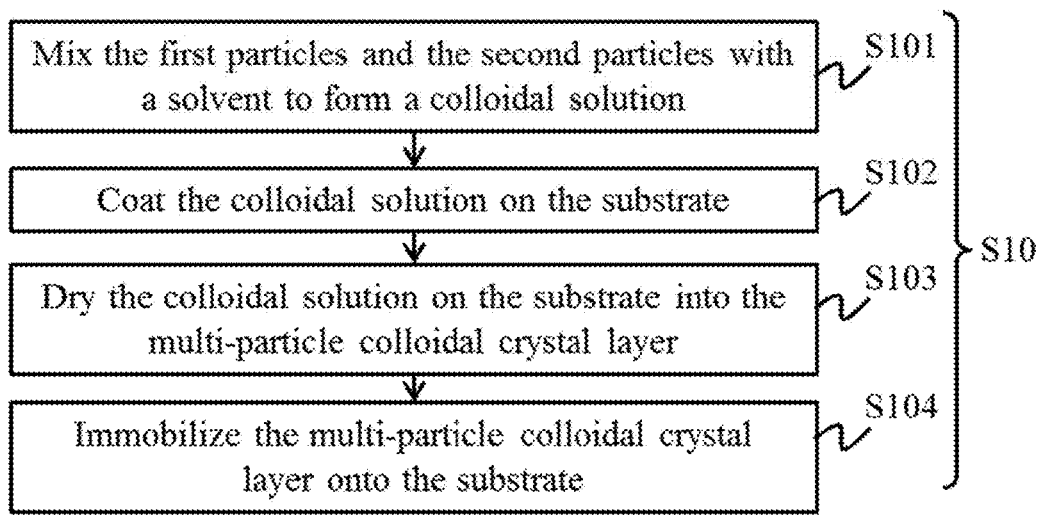
FIG. 7 is a detailed flow chart of an example of Step S10 in FIG. 1.

Referring to FIG. 7, in some embodiments of Step S1, the first particles and the second particles are mixed with a solvent to form a colloidal solution (Step S101), and then the colloidal solution is coated on the two-dimensional planar surface 110 of the substrate 11 (Step S102). Next, the colloidal solution on the substrate 11 is dried under room temperature, to dry the colloidal solution into the multi-particle colloidal crystal layer 12 (Step S103). Afterwards, the multi-particle colloidal crystal layer 12 on the substrate 11 is heated such that the multi-particle colloidal crystal layer 12 is immobilized onto the two-dimensional planar surface 110 of the substrate 11 (Step S104). In an embodiment of Step S103, the colloidal solution on the substrate 11 is stood for at least 3 hrs, to allow the colloidal solution to be dried into the multi-particle colloidal crystal layer 12. Here, the drying steps may take place at room temperature or at a high temperature (for example, in an oven). In an embodiment of Step S104, the dried multi-particle colloidal crystal layer 12 may be immobilized on the two-dimensional planar surface 110 by heating or cross-linking. When the immobilization step is carried out by cross-linking, the cross-linking agent used in the immobilization step may include, but is not limited to, for example, toluene, benzene, xylene, methyl ethyl ketone (MEK), chloroform, tetrahydrofuran (THF), dimethylformamide (DMF), or acetone etc.

In an embodiment, the first and second particles may be made from different materials. In another embodiment, the first and second particles may be made from the same material. Specifically, the first and second particles may be made from silicon (Si), polystyrene (PS), carboxylated polystyrene (PSC), polystyrene sulfonic acid (PSS), poly(methyl methacrylate) (PMMA), gelatin, polycaprolactone (PCL), poly (lactic-co-glycolic acid) (PLGA), and any one or two of other alternative polymer materials.

In some embodiments, besides the first and second particles, the multi-particle colloidal crystal layer 12 further comprises one or more additional particles (for example, third particles and/or quaternary particles). The third particles have a particle size different from that of the first particles, and are made from a material different from that of the second particles. Specifically, the third particles may be made from any one of Si, PS, PSC, PSS, PMMA, gelatin, PCL, PLGA, and other alternative polymer materials. The third particles may have a particle size of 20 to 400 nm.

In some embodiments, the culture medium 22 further comprises a basic fibroblast growth factor (bFGF) and an epidermal growth factor (EGF). In some embodiments, the culture medium 22 comprises 10 ng/ml of at least three basic fibroblast growth factors, 10 ng/ml of an epidermal growth factor, and 3%-20% of a platelet lysate. For example, the basal medium in the culture medium 22 is DMEM/F12 medium, and a basic fibroblast growth factor, epidermal growth factors and a platelet lysate are added to the DMEM/F12 medium to give a concentration of 10 ng/ml, 10 ng/ml, and 10% respectively, thus obtaining the culture medium 22. Here, the platelet lysate may be human platelet lysate. In some embodiments, the culture medium 22 may further comprise an additional supplement, for example, B27 supplement.

Figure 8:
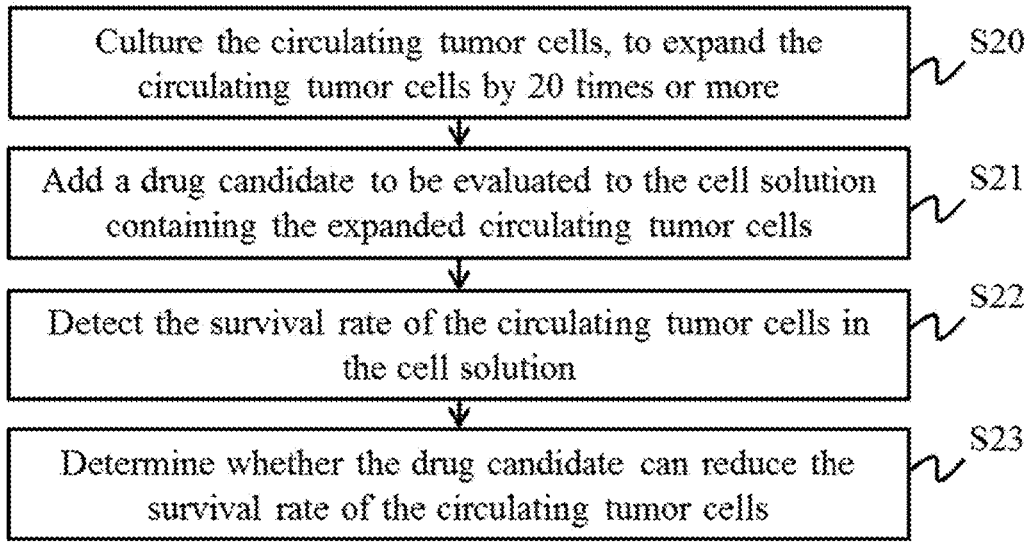
FIG. 8 is a flow chart of a method for screening drugs.

In some embodiments, the cell culture tool 10 and culture medium materials for formulating the culture medium 22 are taken as an integral kit or as main particles in a kit. For example, a kit for expanding circulating tumor cells in vitro comprises the cell culture tool 10 and culture medium materials for formulating the culture medium 22. The cell culture tool 10 and the culture medium materials may be packed in a package. Here, the kit for expanding circulating tumor cells in vitro can be used for culturing the circulating tumor cells 21 which are then used in the screening and evaluation of drugs. For example, referring to FIG. 8, the circulating tumor cells 21 are cultured by using the method for in-vitro expanding circulating tumor cells and/or the kit for in-vitro expanding circulating tumor cells, such that the circulating tumor cells 21 are rapidly expanded by 20 times or more (Step S20). In an embodiment of Step S20, the culture medium materials in the kit for expanding circulating tumor cells in vitro are used to formulate the culture medium 22 containing a platelet lysate, and then the circulating tumor cells 21 are mixed with the formulated culture medium 22 to form the cell solution 20. Afterwards, the cell solution 20 is placed in the cell culture tool 10 of the kit for expanding circulating tumor cells in vitro for culturing, until the circulating tumor cells 21 are expanded by 20 times or more.

After culturing (Step S20), a drug candidate to be evaluated is added to the cell solution 20 containing the expanded circulating tumor cells 21 (Step S21), and then the survival rate of the circulating tumor cells 21 in the cell solution 20 is detected (Step S22). Finally, whether the drug candidate can reduce the survival rate of the circulating tumor cells 21 is determined (Step S23). Here, after the evaluation procedure, the selected drug candidate can be used as a preferred drug candidate or a drug for treating corresponding cancers.

In some embodiments, the circulating tumor cells 21 are the tumor cells derived from small cell lung cancer, lung cancer, breast cancer, pancreatic cancer, liver cancer, sarcoma, melanoma, esophagus cancer, colorectal cancer or nasopharyngeal carcinoma.

The preparation of the cell culture tool 10 of various particle combinations is described below by way of examples. Here, the substrate of the cell culture tool 10 is a common culture plate. Here, two or three kinds of particles are selected according to the particle combinations shown in Table 1 below, and then mixed into a colloidal solution. Next, the colloidal solution is positioned in a well of a common culture plate, and stood overnight (that is, for at least 12 hrs) to air dry the colloidal solution. Afterwards, the air-dried culture plate is heated in an oven, to volatilize the water in the colloidal solution, that is, to form the multi-particle colloidal crystal layer 12, and immobilize the multi-particle colloidal crystal layer 12 on a bottom surface of the well of the culture plate.

TABLE 1

| First particles | | Second particles | | Third particles | |
| --- | --- | --- | --- | --- | --- |
| Material | Particle size (nm) | Material | Particle size (nm) | Material | Particle size (nm) |
| Si | 2000 | PS | 65 | — | — |
| Si | 2000 | PS | 100 | — | — |
| Si | 2000 | PSC | 24 | — | — |
| Si | 2000 | PSC | 65 | — | — |
| Si | 2000 | PSC | 93 | — | — |
| Si | 2000 | PSC | 100 | — | — |
| Si | 2000 | PSC | 200 | — | — |
| Si | 2000 | PSC | 220 | — | — |
| Si | 2000 | PM | 68 | — | — |
| Si | 2000 | PM | 100 | — | — |
| Si | 2000 | PMMA | 100 | — | — |
| Si | 2000 | PMMA | 400 | — | — |
| Si | 2000 | PLGA | 200 | — | — |
| Si | 2000 | PCL | 200 | — | — |
| Si | 2000 | gelatin | 200 | — | — |
| Si | 5000 | PS | 65 | — | — |
| Si | 5000 | PS | 200 | — | — |
| Si | 5000 | PS | 400 | — | — |
| Si | 5000 | PSC | 100 | — | — |
| Si | 5000 | PSC | 400 | — | — |
| Si | 5000 | PM | 68 | — | — |
| Si | 5000 | PM | 100 | — | — |
| Si | 5000 | PM | 400 | — | — |
| Si | 5000 | PMMA | 100 | — | — |
| Si | 5000 | PMMA | 400 | — | — |
| PS | 2000 | PSC | 100 | — | — |
| PS | 2000 | PSC | 220 | — | — |
| PS | 2000 | PMMA | 400 | — | — |
| PSC | 2000 | PSC | 22 | — | — |
| PSC | 2000 | PSC | 93 | — | — |
| PSC | 2000 | PMMA | 400 | — | — |
| PSS | 2000 | PSC | 24 | — | — |
| Si | 2000 | PMMA | 400 | PSC | 93 |
| PSC | 2000 | PMMA | 400 | PSC | 60 |

The formed multi-particle colloidal crystal layer is observed under a scanning electron microscope, as shown in FIGS. 9A to 36.

Figure 9A:
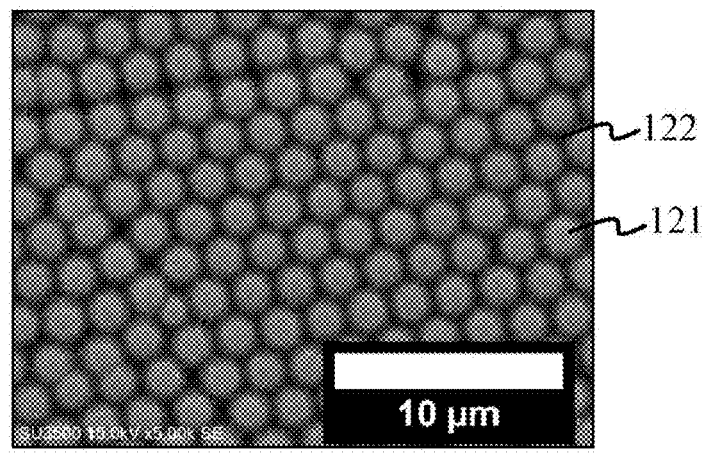
FIG. 9A and FIG. 9B are Scanning Electron Microscope (SEM) images of the surface of a multi-particle colloidal crystal layer according to Example 1.
Figure 9B:
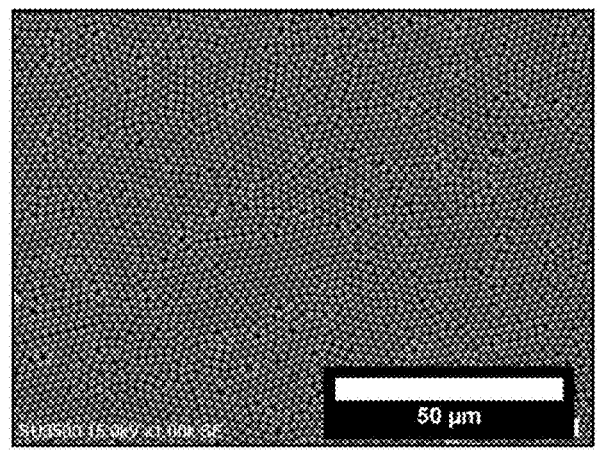
Figure 10A:
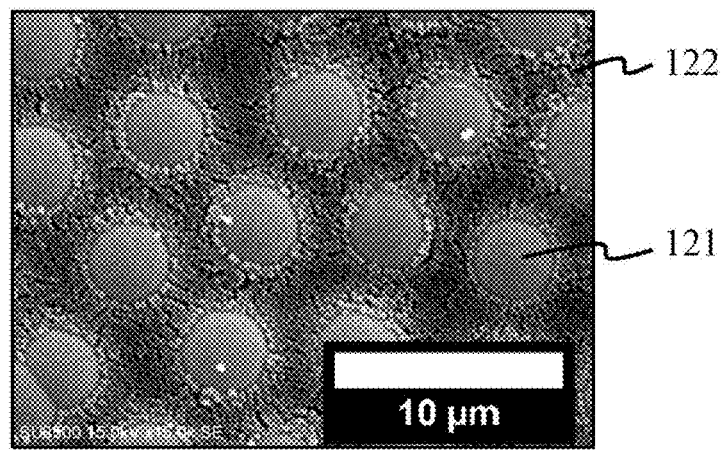
FIG. 10A and FIG. 10B are SEM images of the surface of a multi-particle colloidal crystal layer according to Example 2.
Figure 10B:
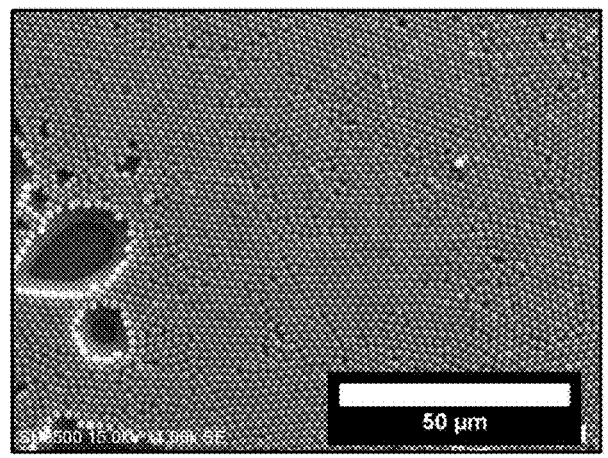
Figure 11:
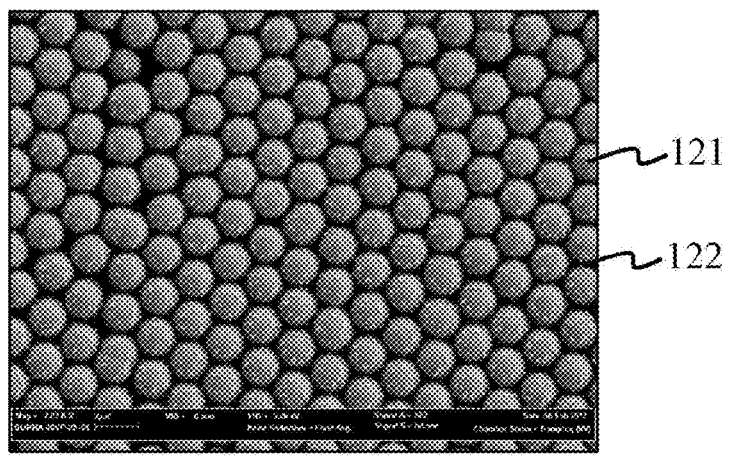
FIG. 11 is an SEM image of the surface of a multi-particle colloidal crystal layer according to Example 3.
Figure 12A:
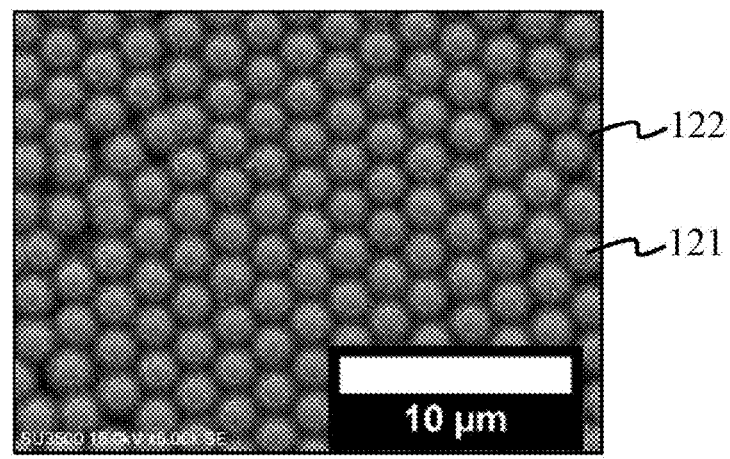
FIG. 12A and FIG. 12B are SEM images of the surface of a multi-particle colloidal crystal layer according to Example 4.
Figure 12B:
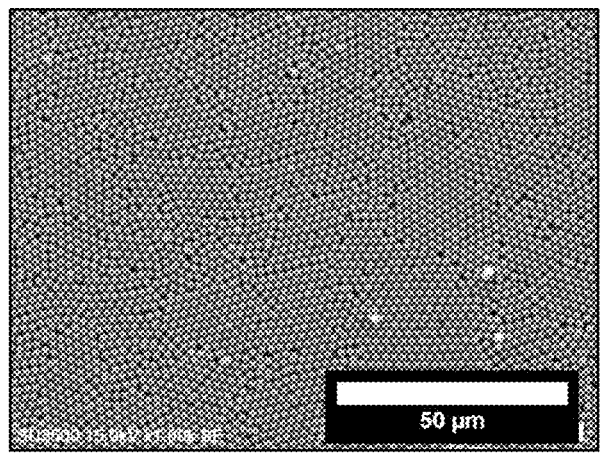
Figure 13:
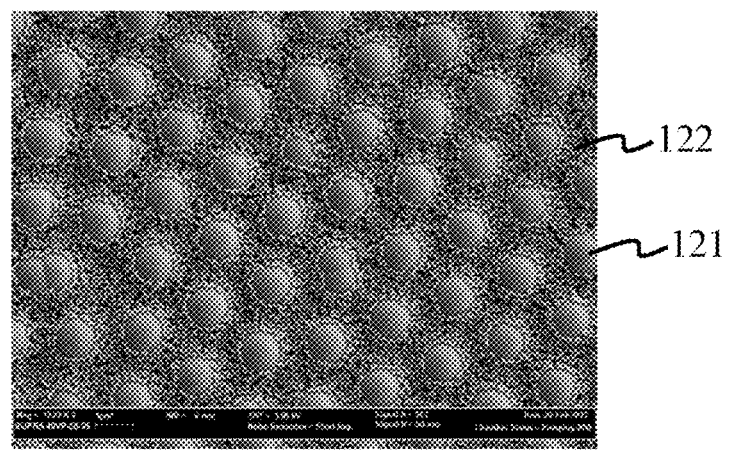
FIG. 13 is an SEM image of the surface of a multi-particle colloidal crystal layer according to Example 5.
Figure 14A:
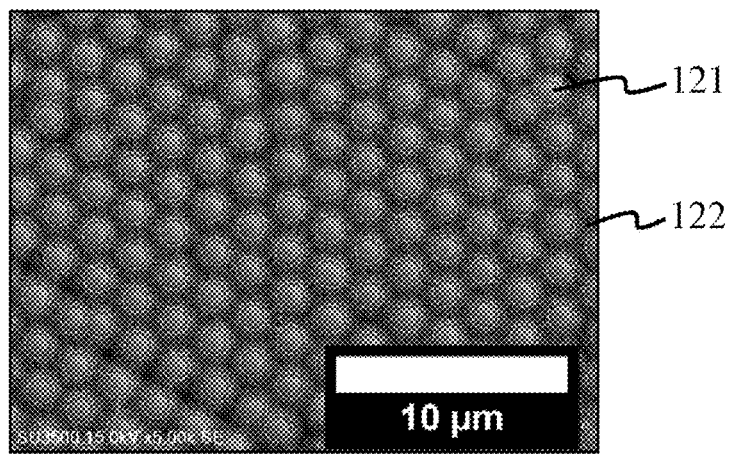
FIG. 14A and FIG. 14B are SEM images of the surface of a multi-particle colloidal crystal layer according to Example 6.
Figure 14B:
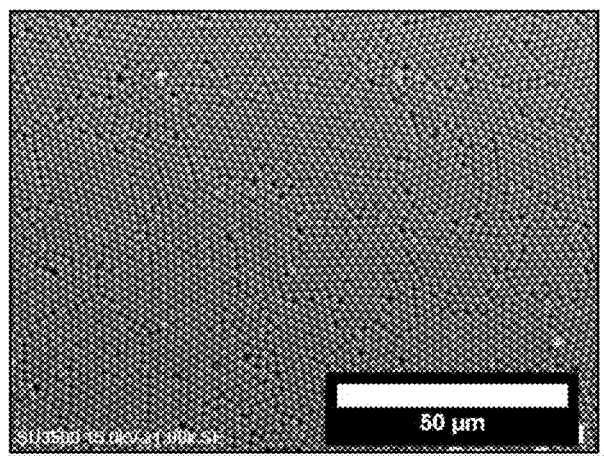
Figure 15A:
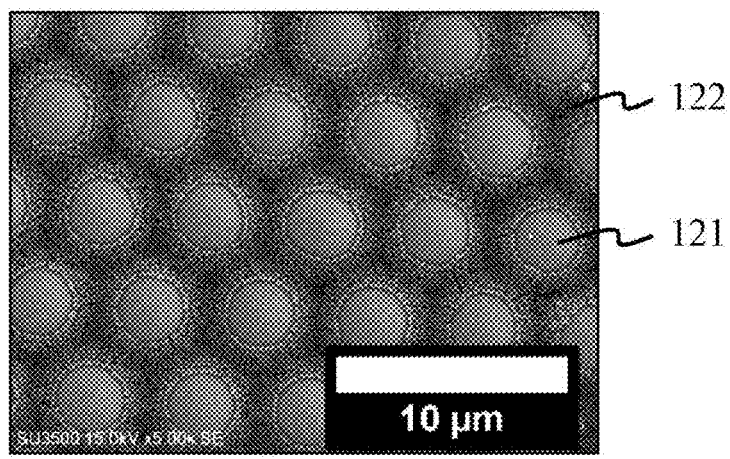
FIG. 15A and FIG. 15B are SEM images of the surface of a multi-particle colloidal crystal layer according to Example 7.
Figure 15B:
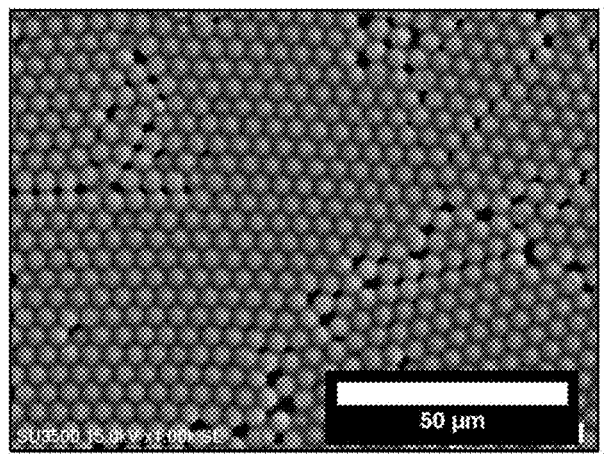
Figure 16:
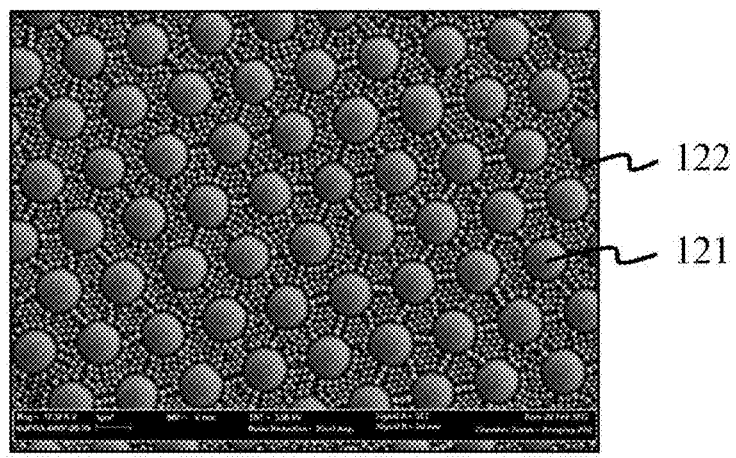
FIG. 16 is an SEM image of the surface of a multi-particle colloidal crystal layer according to Example 8.
Figure 17A:
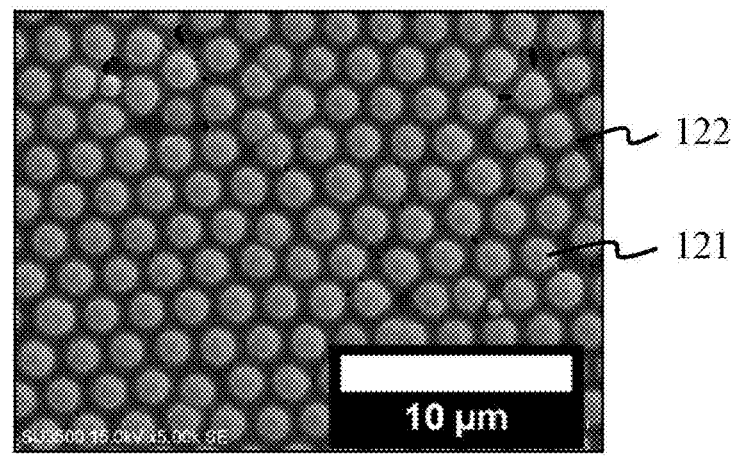
FIG. 17A and FIG. 17B are SEM images of the surface of a multi-particle colloidal crystal layer according to Example 9.
Figure 17B:
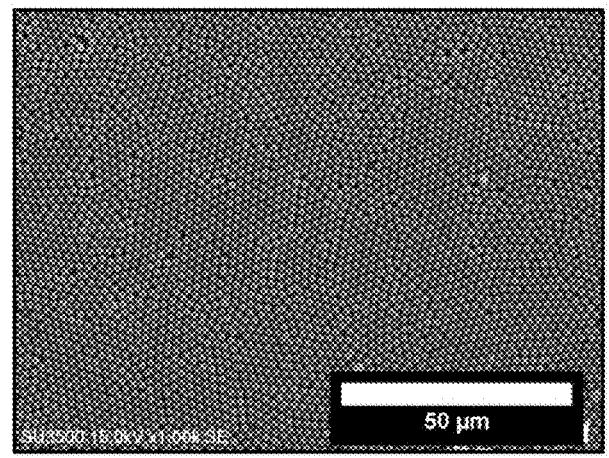
Figure 18A:
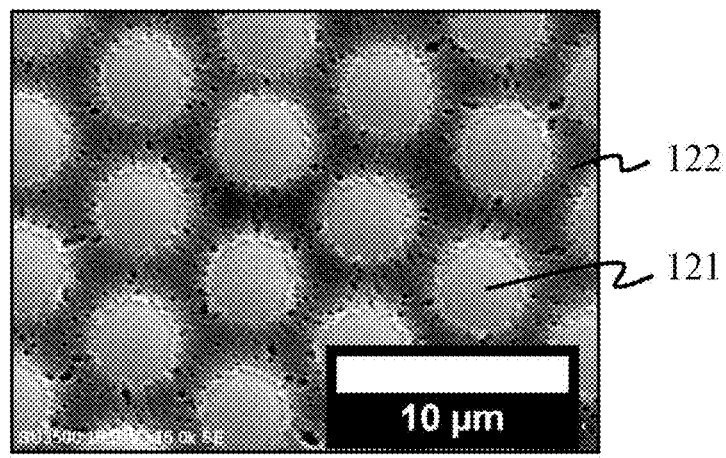
FIG. 18A and FIG. 18B are SEM images of the surface of a multi-particle colloidal crystal layer according to Example 10.
Figure 18B:
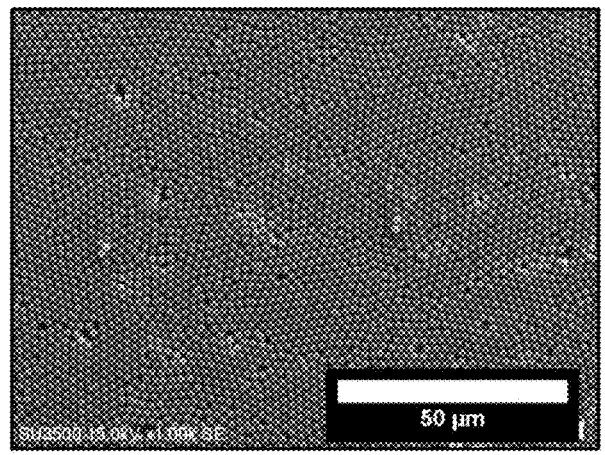
Figure 19:
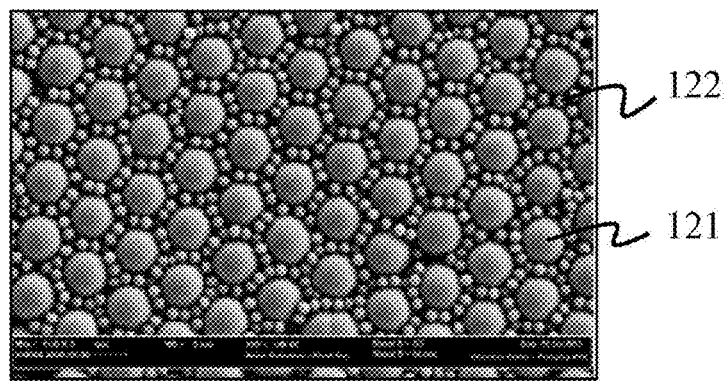
FIG. 19 is an SEM image of the surface of a multi-particle colloidal crystal layer according to Example 11.
Figure 20:
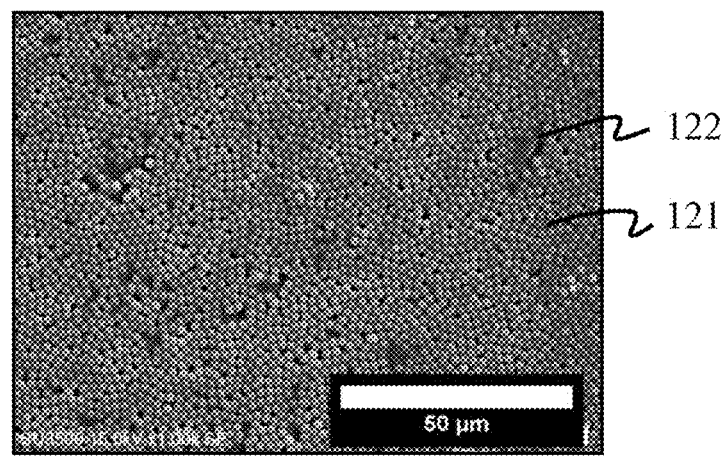
FIG. 20 is an SEM image of the surface of a multi-particle colloidal crystal layer according to Example 12.
Figure 21:
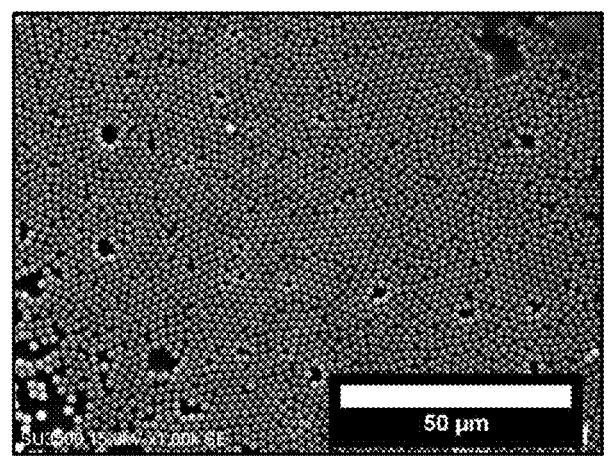
FIG. 21 is an SEM image of the surface of a multi-particle colloidal crystal layer according to Example 13.
Figure 22:
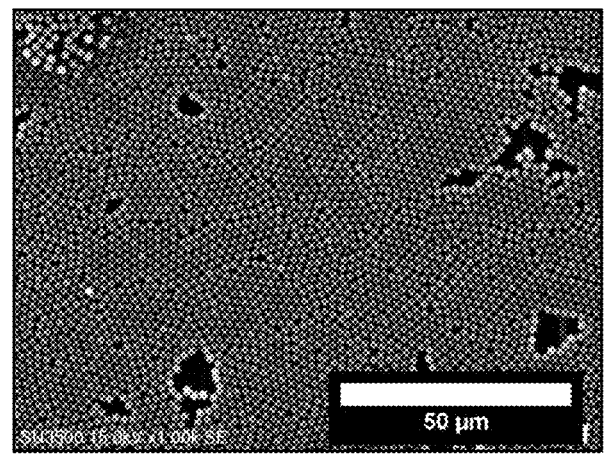
FIG. 22 is an SEM image of the surface of a multi-particle colloidal crystal layer according to Example 14.
Figure 23A:
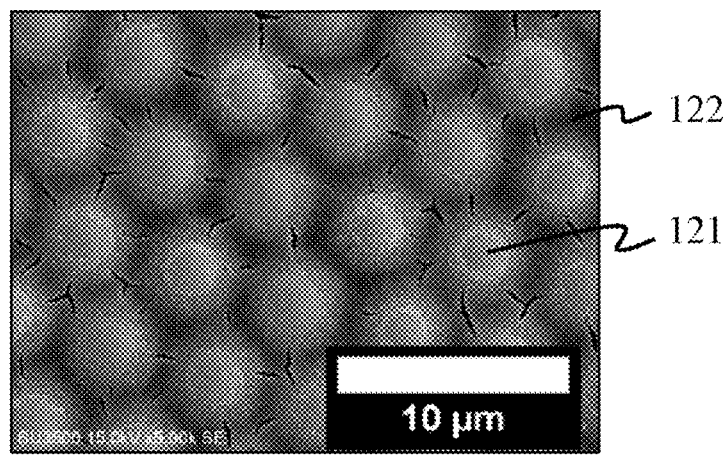
FIG. 23A and FIG. 23B are SEM images of the surface of a multi-particle colloidal crystal layer according to Example 15.
Figure 23B:
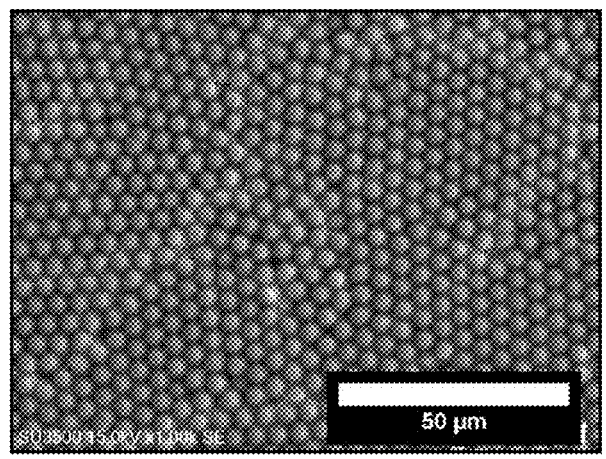
Figure 24A:
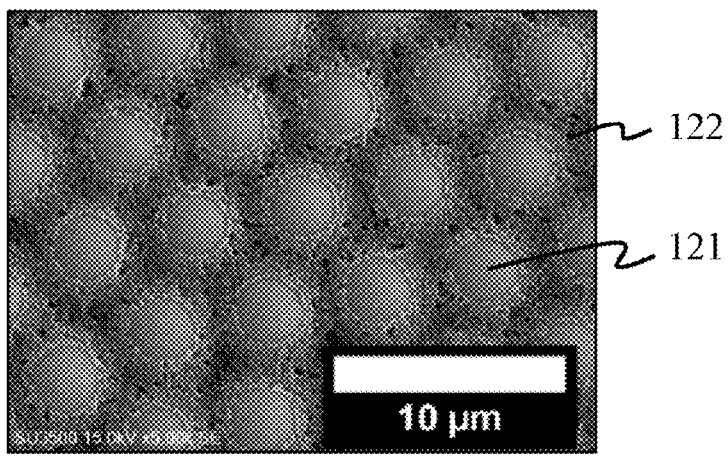
FIG. 24A and FIG. 24B are SEM images of the surface of a multi-particle colloidal crystal layer according to Example 16.
Figure 24B:
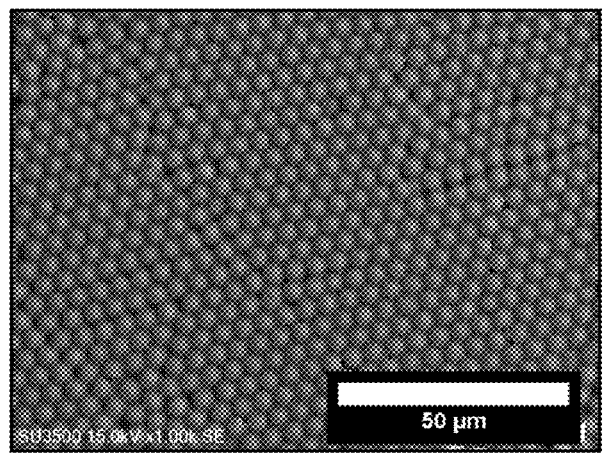
Figure 25A:
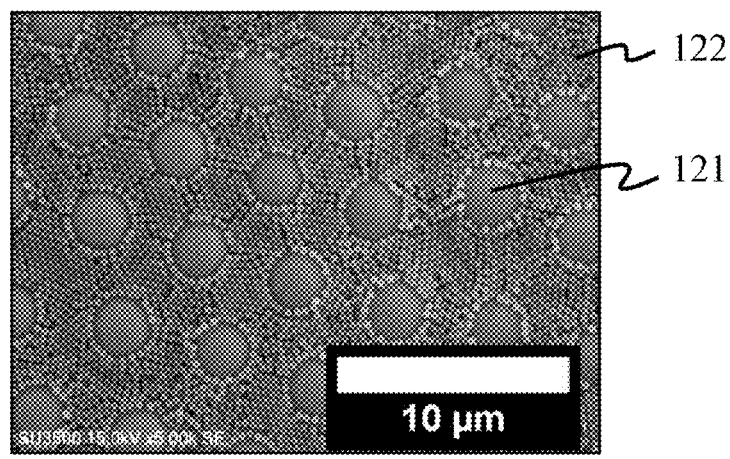
FIG. 25A and FIG. 25B are SEM images of the surface of a multi-particle colloidal crystal layer according to Example 17.
Figure 25B:
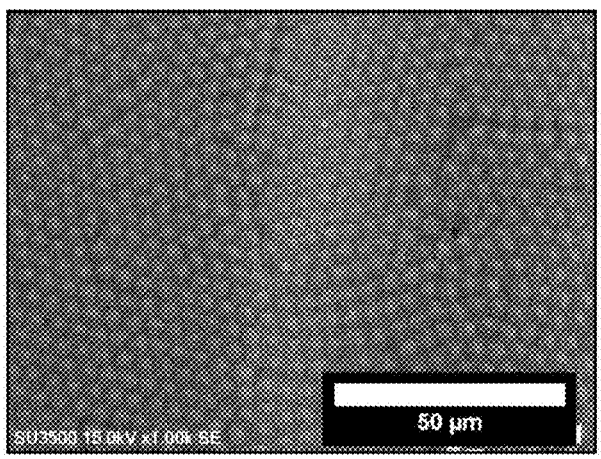
Figure 26A:
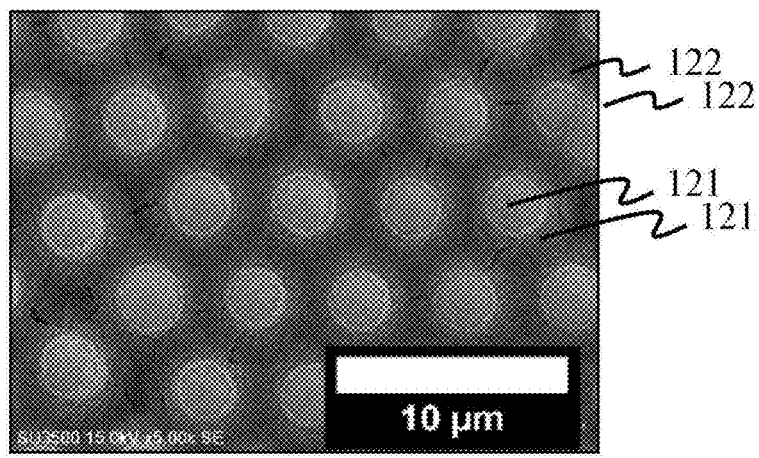
FIG. 26A and FIG. 26B are SEM images of the surface of a multi-particle colloidal crystal layer according to Example 18.
Figure 26B:
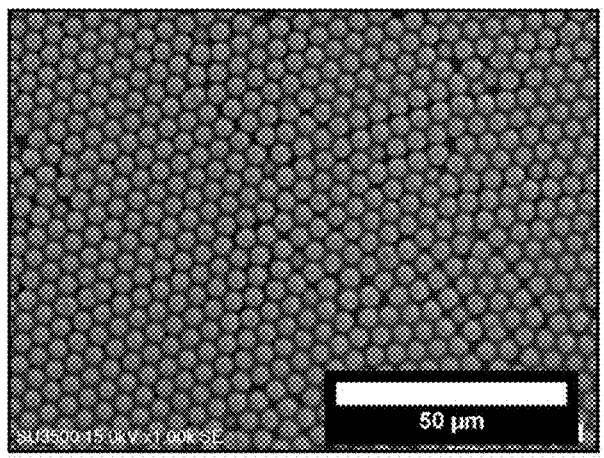
Figure 27A:
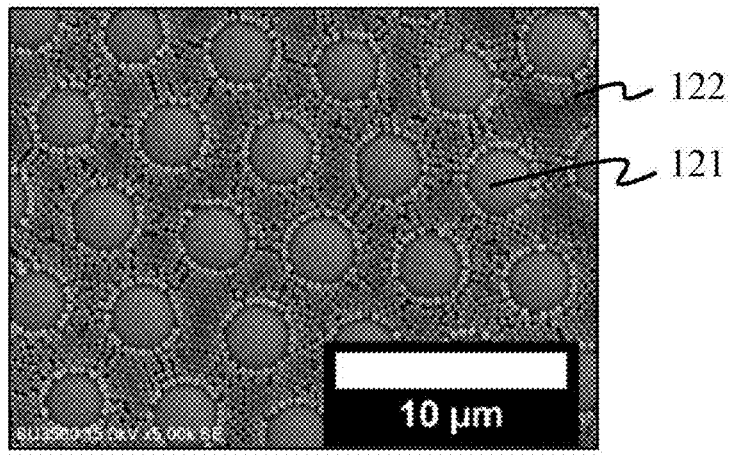
FIG. 27A and FIG. 27B are SEM images of the surface of a multi-particle colloidal crystal layer according to Example 19.
Figure 27B:
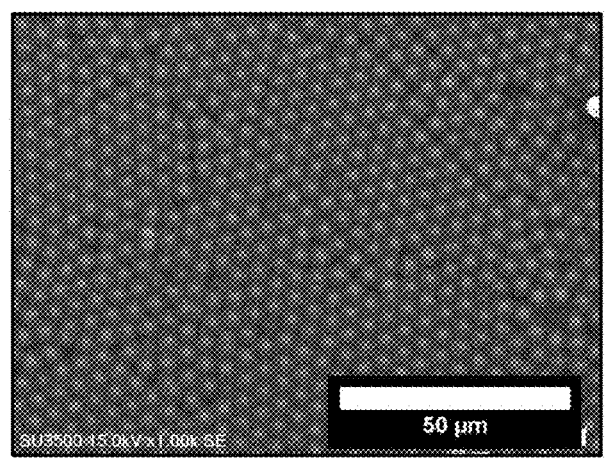
Figure 28A:
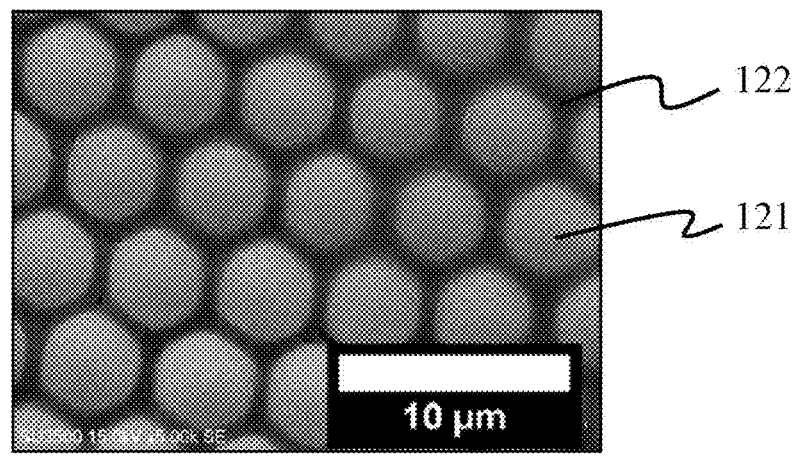
FIG. 28A and FIG. 28B are SEM images of the surface of a multi-particle colloidal crystal layer according to Example 20.
Figure 28B:
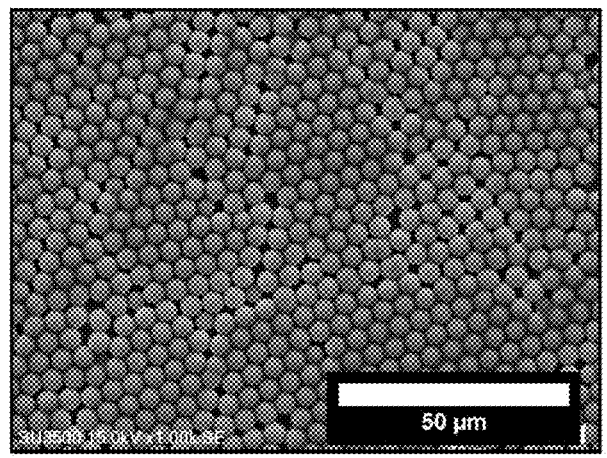
Figure 29A:
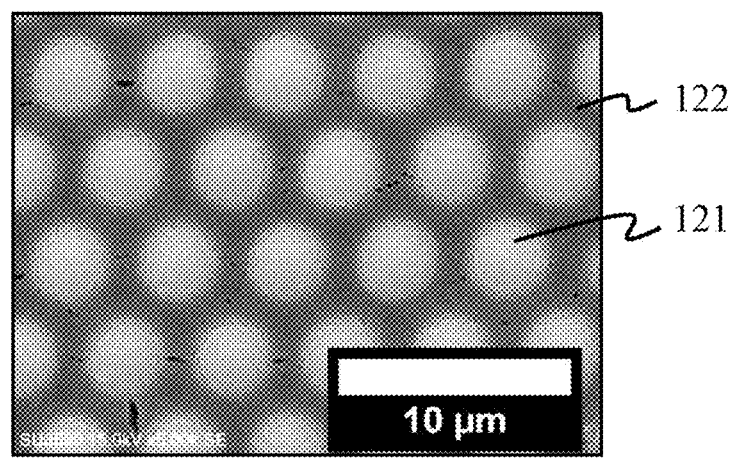
FIGS. 29A and 29B are SEM images of the surface of a multi-particle colloidal crystal layer according to Example 21.
Figure 29B:
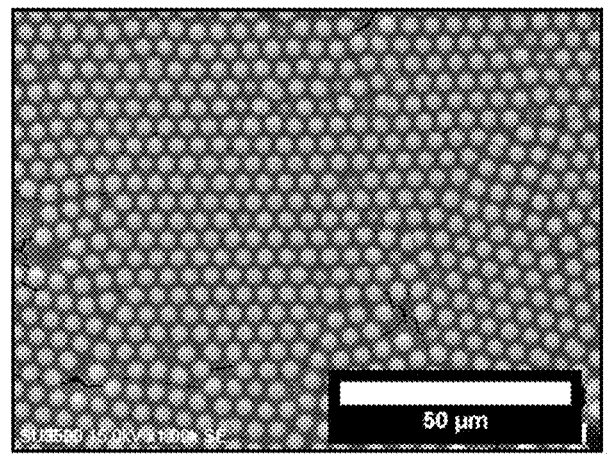
Figure 30A:
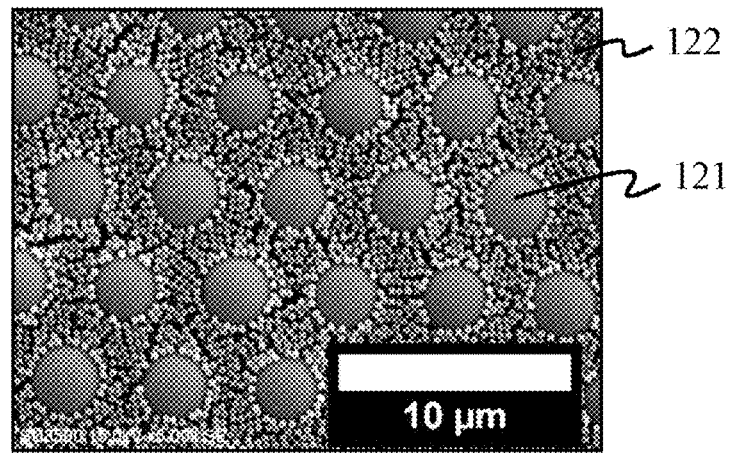
FIGS. 30A and 30B are SEM images of the surface of a multi-particle colloidal crystal layer according to Example 22.
Figure 30B:
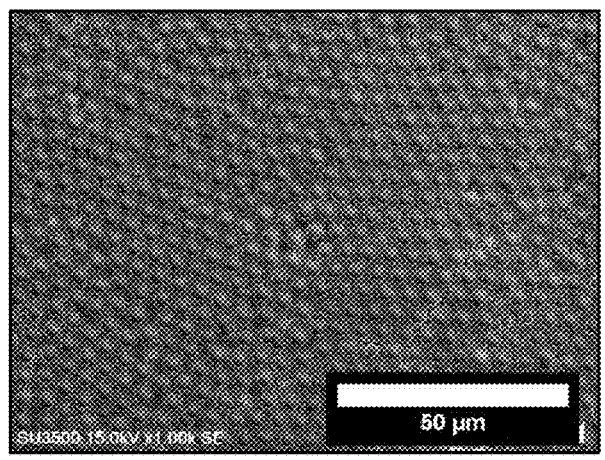
Figure 31:
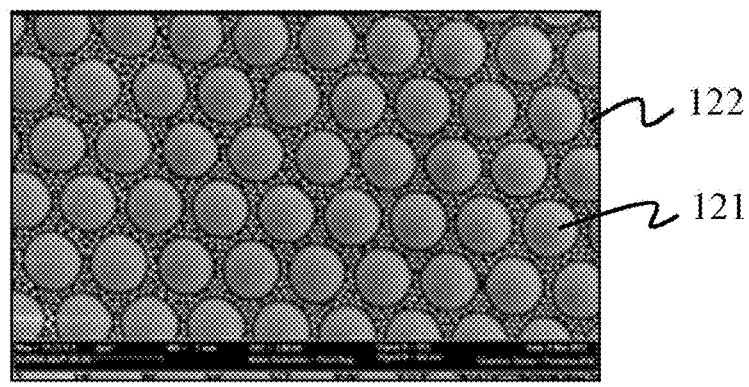
FIG. 31 is an SEM image of the surface of a multi-particle colloidal crystal layer according to Example 23.
Figure 32:
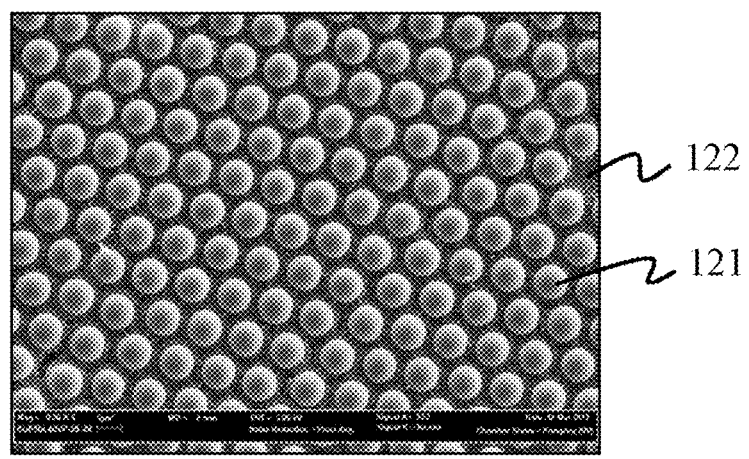
FIG. 32 is an SEM image of the surface of a multi-particle colloidal crystal layer according to Example 24.
Figure 33:
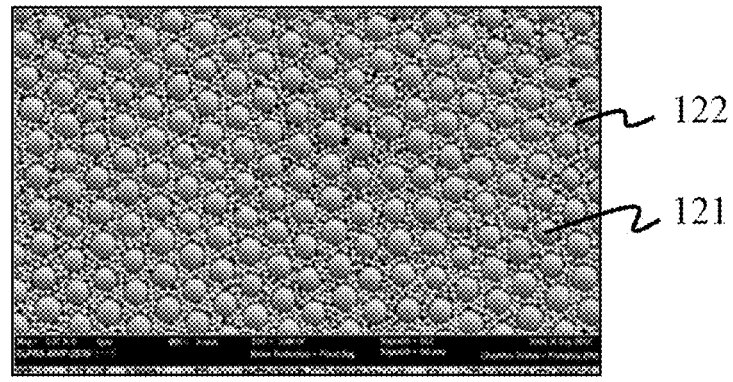
FIG. 33 is an SEM image of the surface of a multi-particle colloidal crystal layer according to Example 25.
Figure 34:
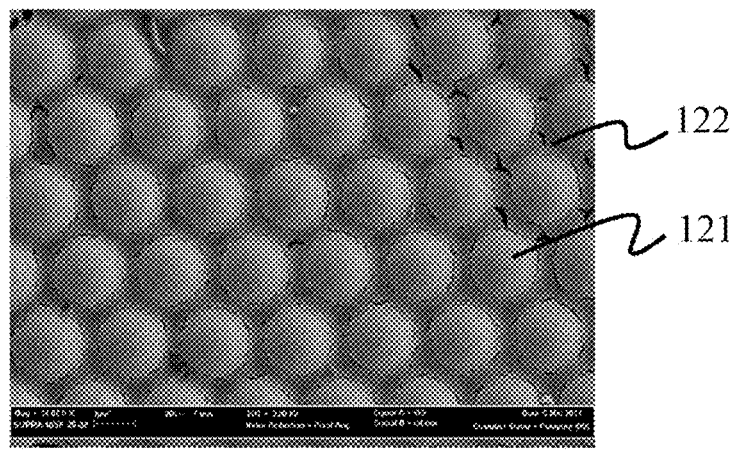
FIG. 34 is an SEM image of the surface of a multi-particle colloidal crystal layer according to Example 26.
Figure 35:
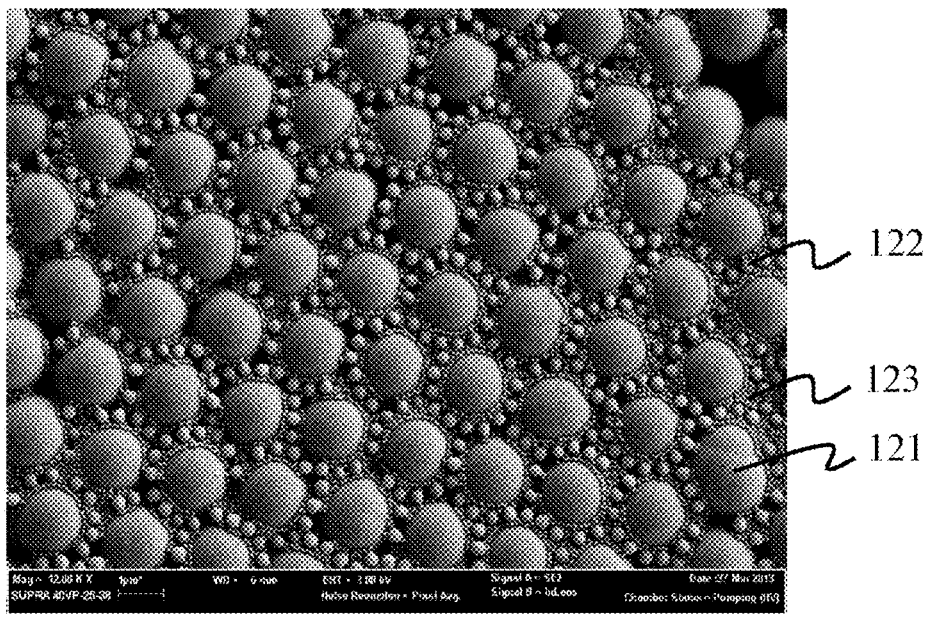
FIG. 35 is an SEM image of the surface of a multi-particle colloidal crystal layer according to Example 27.
Figure 36:
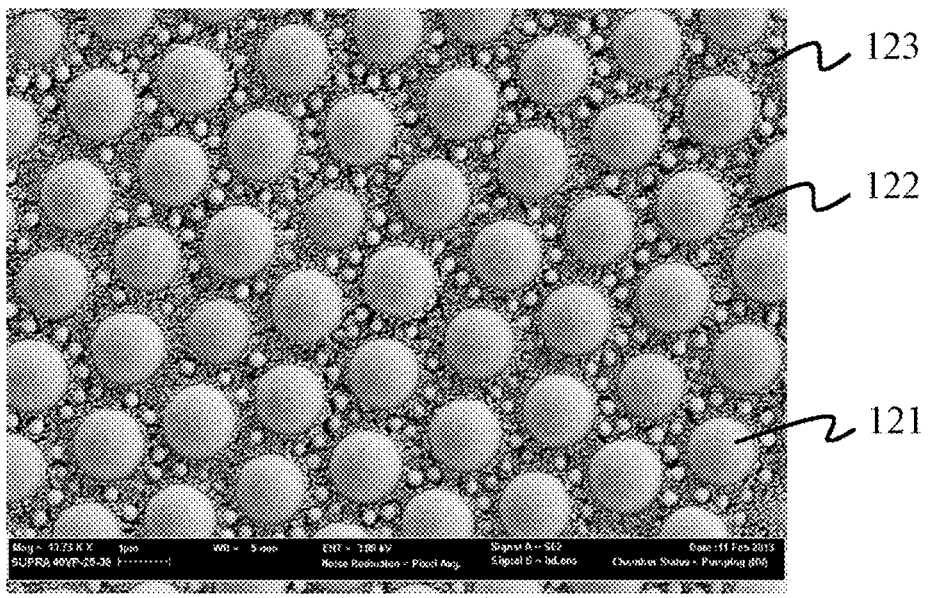
FIG. 36 is an SEM image of the surface of a multi-particle colloidal crystal layer according to Example 28.

FIGS. 9A and 9B show a multi-particle colloidal crystal layer formed by Si particles having a particle size of 2000 nm (that is, first particles 121) and PS particles having a particle size of 65 nm (that is, second particles 122). FIGS. 10A and 10B show a multi-particle colloidal crystal layer formed by Si particles having a particle size of 2000 nm (that is, first particles 121) and PS particles having a particle size of 100 nm (that is, second particles 122). FIG. 11 shows a multi-particle colloidal crystal layer formed by Si particles having a particle size of 2000 nm (that is, first particles 121) and PSC particles having a particle size of 24 nm (that is, second particles 122). FIGS. 12A and 12B show a multi-particle colloidal crystal layer formed by Si particles having a particle size of 2000 nm (that is, first particles 121) and PSC particles having a particle size of 65 nm (that is, second particles 122). FIG. 13 shows a multi-particle colloidal crystal layer formed by Si particles having a particle size of 2000 nm (that is, first particles 121) and PSC particles having a particle size of 93 nm (that is, second particles 122). FIGS. 14A and 14B show a multi-particle colloidal crystal layer formed by Si particles having a particle size of 2000 nm (that is, first particles 121) and PSC particles having a particle size of 100 nm (that is, second particles 122). FIGS. 15A and 15B show a multi-particle colloidal crystal layer formed by Si particles having a particle size of 2000 nm (that is, first particles 121) and PSC particles having a particle size of 200 nm (that is, second particles 122). FIG. 16 shows a multi-particle colloidal crystal layer formed by Si particles having a particle size of 2000 nm (that is, first particles 121) and PSC particles having a particle size of 220 nm (that is, second particles 122). FIGS. 17A and 17B show a multi-particle colloidal crystal layer formed by Si particles having a particle size of 2000 nm (that is, first particles 121) and PM particles having a particle size of 68 nm (that is, second particles 122). FIGS. 18A and 18B show a multi-particle colloidal crystal layer formed by Si particles having a particle size of 2000 nm (that is, first particles 121) and PM particles having a particle size of 100 nm (that is, second particles 122). FIG. 19 shows a multi-particle colloidal crystal layer formed by Si particles having a particle size of 2000 nm (that is, first particles 121) and PMMA particles having a particle size of 400 nm (that is, second particles 122). FIG. 20 shows a multi-particle colloidal crystal layer formed by Si particles having a particle size of 2000 nm (that is, first particles 121) and PLGA particles having a particle size of 200 nm (that is, second particles 122). FIG. 21 shows a multi-particle colloidal crystal layer formed by Si particles having a particle size of 2000 nm (that is, first particles 121) and PCL particles having a particle size of 200 nm (that is, second particles 122). FIG. 22 shows a multi-particle colloidal crystal layer formed by Si particles having a particle size of 2000 nm (that is, first particles 121) and gelatin particles having a particle size of 200 nm (that is, second particles 122). FIGS. 23A and 23B show a multi-particle colloidal crystal layer formed by Si particles having a particle size of 5000 nm (that is, first particles 121) and PS particles having a particle size of 65 nm (that is, second particles 122). FIGS. 24A and 24B shows a multi-particle colloidal crystal layer formed by Si particles having a particle size of 5000 nm (that is, first particles 121) and PS particles having a particle size of 200 nm (that is, second particles 122). FIGS. 25A and 25B show a multi-particle colloidal crystal layer formed by Si particles having a particle size of 5000 nm (that is, first particles 121) and PS particles having a particle size of 400 nm (that is, second particles 122). FIGS. 26A and 26B show a multi-particle colloidal crystal layer formed by Si particles having a particle size of 5000 nm (that is, first particles 121) and PSC particles having a particle size of 100 nm (that is, second particles 122). FIGS. 27A and 27B show a multi-particle colloidal crystal layer formed by Si particles having a particle size of 5000 nm (that is, first particles 121) and PSC particles having a particle size of 400 nm (that is, second particles 122). FIGS. 28A and 28B show a multi-particle colloidal crystal layer formed by Si particles having a particle size of 5000 nm (that is, first particles 121) and PM particles having a particle size of 68 nm (that is, second particles 122). FIGS. 29A and 29B show a multi-particle colloidal crystal layer formed by Si particles having a particle size of 5000 nm (that is, first particles 121) and PM particles having a particle size of 100 nm (that is, second particles 122). FIGS. 30A and 30B show a multi-particle colloidal crystal layer formed by Si particles having a particle size of 5000 nm (that is, first particles 121) and PM particles having a particle size of 400 nm (that is, second particles 122). FIG. 31 shows a multi-particle colloidal crystal layer formed by PSC particles having a particle size of 2000 nm (that is, first particles 121) and PSC particles having a particle size of 22 nm (that is, second particles 122). FIG. 32 shows a multi-particle colloidal crystal layer formed by PSC particles having a particle size of 2000 nm (that is, first particles 121)PSC particles having a particle size of 93 nm (that is, second particles 122). FIG. 33 shows a multi-particle colloidal crystal layer formed by PSC particles having a particle size of 2000 nm (that is, first particles 121) and PMMA particles having a particle size of 400 nm (that is, second particles 122). FIG. 34 shows a multi-particle colloidal crystal layer formed by PSS particles having a particle size of 2000 nm (that is, first particles 121) and PSC particles having a particle size of 24 nm (that is, second particles 122). FIG. 35 shows a multi-particle colloidal crystal layer formed by Si particles having a particle size of 2000 nm (that is, first particles 121), PMMA particles having a particle size of 400 nm (that is, second particles 122) and PSC particles having a particle size of 93 nm FIG. 36 shows a multi-particle colloidal crystal layer formed by PSC particles having a particle size of 2000 nm (that is, first particles 121), PMMA particles having a particle size of 400 nm (that is, third particles 123), and PSC particles having a particle size of 93 nm.

In some embodiments, the preparation of the cell solution can be performed as follows. 5 ml of blood is sampled respectively patients having breast cancer, pancreatic cancer, and small cell lung cancer. 15 ml of Ficoll-Paque is added to a Leucosep™ centrifuge tube and centrifuged. The blood is diluted in phosphate buffered saline (PBS) and transferred to the Leucosep™ centrifuge tube, followed by centrifugation. After centrifugation, the supernatant in the Leucosep™ centrifuge tube is removed, and the retained lower solution is a monocyte phase. A circulating tumor cell enriched antibody mixture (RosetteSep™ CTC Enrichment Cocktail Containing AntiCD56) is added to the monocyte phase, and mixed at room temperature. After mixing, a PBS buffer containing 2% (v/v) Fetal Bovine Serum (FSB) is added and mixed to give a monocyte solution. Also, the monocyte solution is added to Ficoll-Paque and centrifuged at room temperature. Next, the concentrated cells were removed from the intermediate layer obtained after the centrifugation, and the concentrated cells were washed with a PBS buffer solution containing 2% (v/v) FBS. Here, a concentrated cell solution containing the circulating tumor cells 21 (derived from small cell lung cancer, breast cancer, or pancreatic cancer) is obtained.

The culture medium 22 is added to each well of the cell culture tool 10. Then, the concentrated cell solution containing the circulating tumor cells 21 is added to the culture medium 22 to form the cell solution 20 and then cultured. During the culturing process, some of the circulating tumor cells 21 are attached to the multi-particle colloidal crystal layer 12 and expanded continuously, such that the cell density of the circulating tumor cells 21 in the cell solution 20 reaches $10^6$ cells or higher. The remaining circulating tumor cells 21 are suspended in the culture medium 22.

Figure 37:
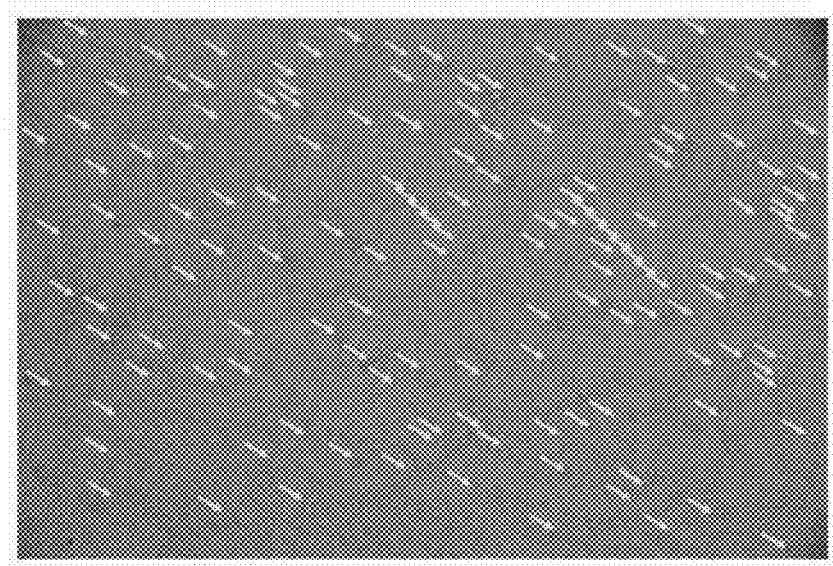
FIG. 37 is an optical micrograph at 200× magnification showing melanoma-derived circulating tumor cells at day 10 after being cultured.
Figure 38:
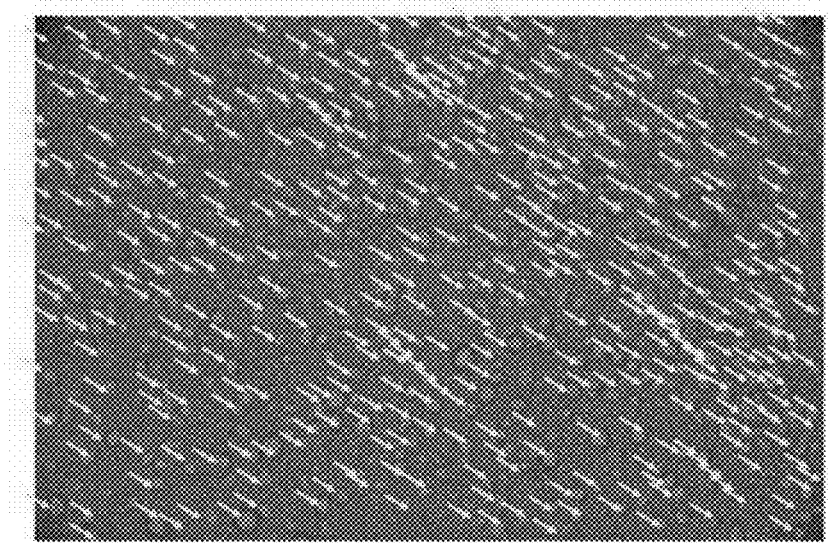
FIG. 38 is an optical micrograph at 200× magnification showing melanoma-derived circulating tumor cells at day 31 after being cultured.

FIGS. 37 and 38 show the growth states of the melanoma-derived circulating tumor cells 21 at days 10 and 31 after being cultured in the cell culture tool 10 shown in FIGS. 25A and 25B according to the above procedure. Here, at day 10 after culturing, the circulating tumor cells 21 are attached to and form a colony on the multi-particle colloidal crystal layer in the cell culture tool 10 (indicated by the arrows), as shown in FIG. 37. At day 31 after culturing, the colonies formed by the circulating tumor cells 21 on the multi-particle colloidal crystal layer in the cell culture tool 10 are increased obviously (indicated by the arrows), as shown in FIG. 38.

Figure 39:
FIG. 39 is an optical micrograph at 100× magnification showing liver cancer-derived circulating tumor cells at day 17 after being cultured.
Figure 40:
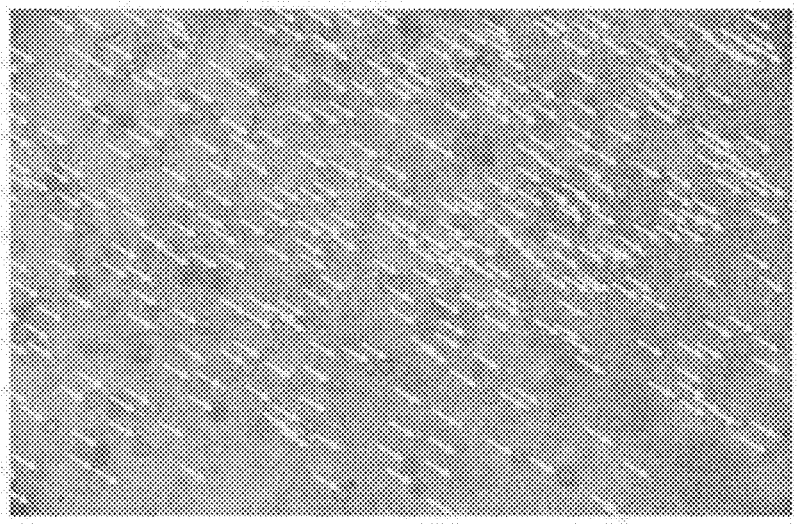
FIG. 40 is an optical micrograph at 100× magnification showing liver cancer-derived circulating tumor cells at day 36 after being cultured.

FIGS. 39 and 40 show the growth states of the liver cancer-derived circulating tumor cells 21 at days 17 and 36 after being cultured in the cell culture tool 10 shown in FIGS. 24A and 24B according to the above procedure. Here, at day 17 after culturing, the circulating tumor cells 21 are attached to and form a colony on the multi-particle colloidal crystal layer in the cell culture tool 10 (indicated by the arrows), as shown in FIG. 39. At day 36 after culturing, the colonies formed by the circulating tumor cells 21 on the multi-particle colloidal crystal layer in the cell culture tool 10 are increased obviously (indicated by the arrows), as shown in FIG. 40.

Figure 41:
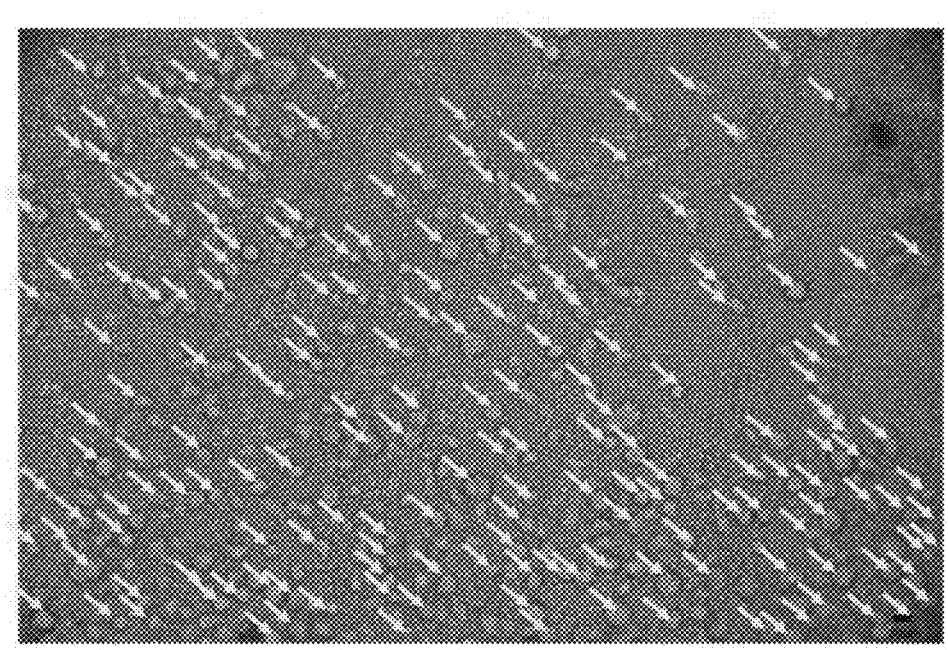
FIG. 41 is an optical micrograph showing breast cancer-derived circulating tumor cells cultured through the method for expanding circulating tumor cells in vitro according to an embodiment of the present invention.
Figure 42:
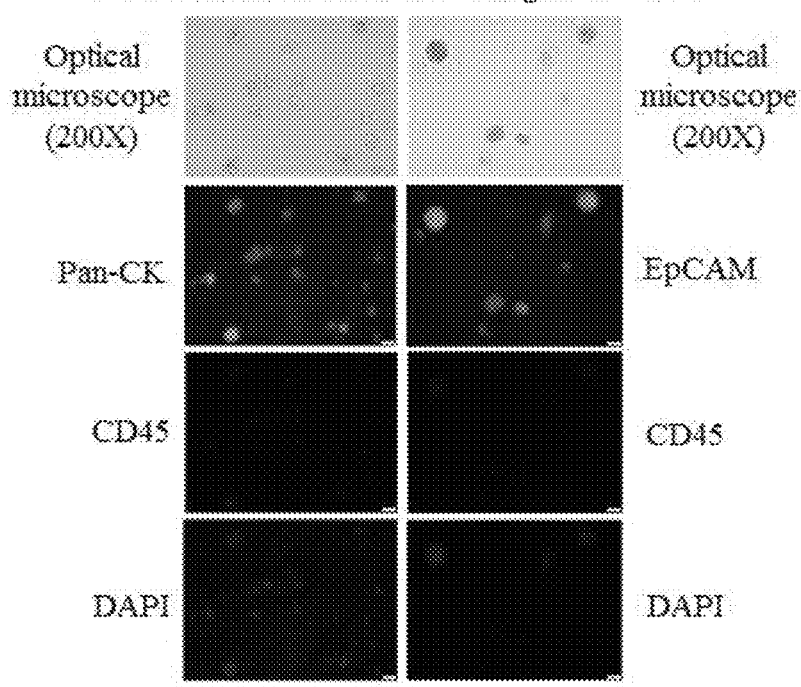
FIG. 42 shows immunofluorescence staining images of Pan-CK, CD45, and 4',6-diamidino-2-phenylindole (DPAI) in breast cancer-derived circulating tumor cells as shown in FIG. 41.
Figure 43:
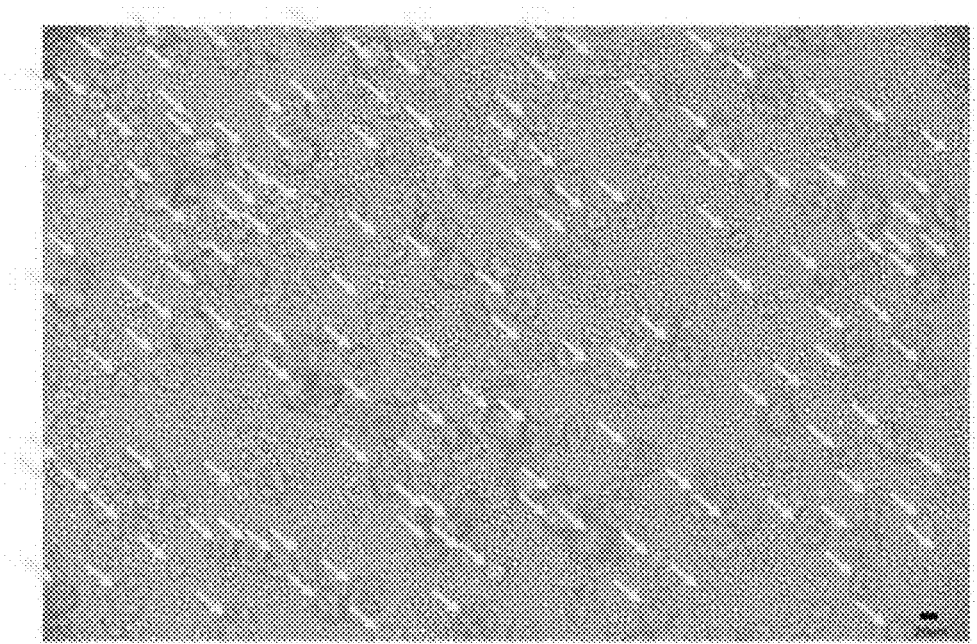
FIG. 43 is an optical micrograph showing pancreatic cancer-derived circulating tumor cells cultured through the method for expanding circulating tumor cells in vitro according to an embodiment of the present invention.
Figure 44:
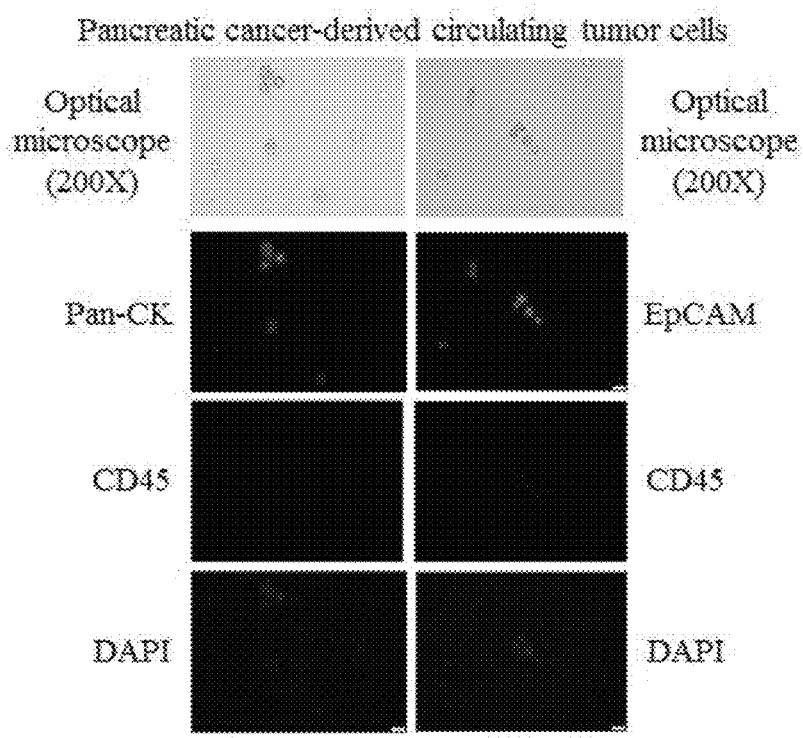
FIG. 44 shows immunofluorescence staining images of Pan-CK, CD45, and DPAI in pancreatic cancer-derived circulating tumor cells as shown in FIG. 43.
Figure 45:
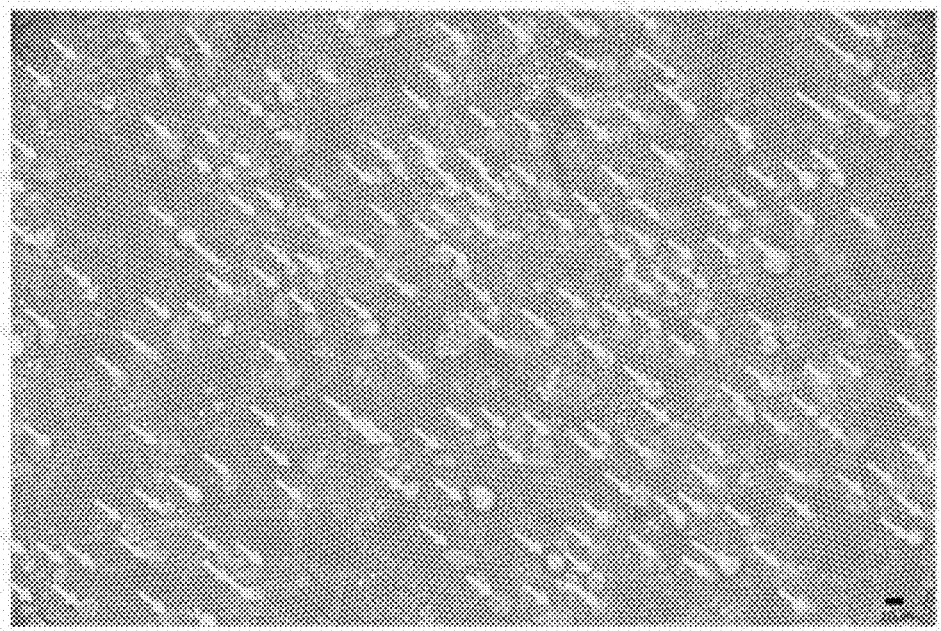
FIG. 45 shows small cell lung cancer-derived circulating tumor cells cultured through the method for expanding circulating tumor cells in vitro according to an embodiment of the present invention.
Figure 46:
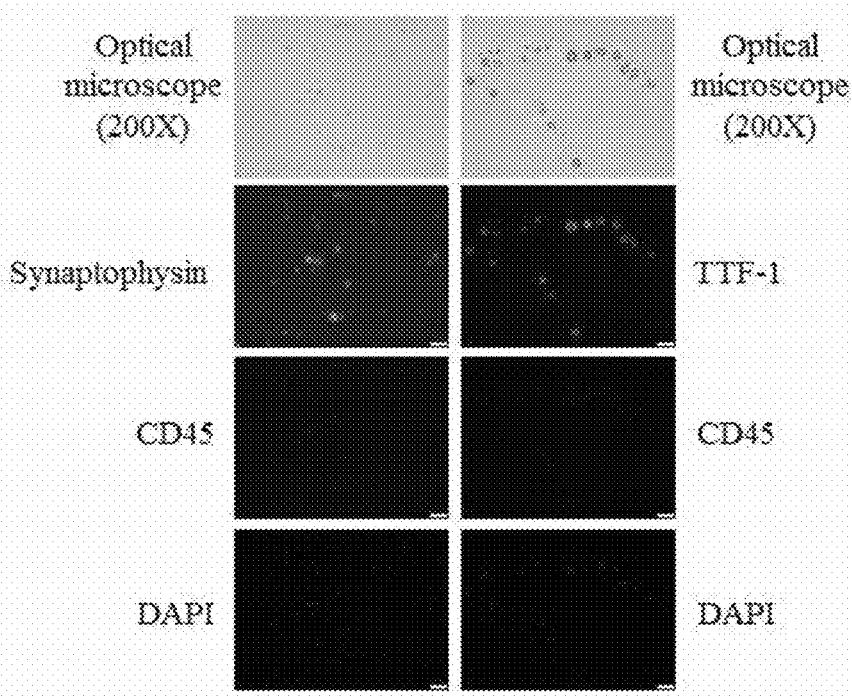
FIG. 46 shows immunofluorescence staining images of synaptophysin, thyroid transcription factor-1 (TTF-1), CD45, and DPAI in the small cell lung cancer-derived circulating tumor cells as shown in FIG. 45.

FIGS. 41 and 42 show the growth states of the breast cancer-derived circulating tumor cells 21 at day 17 after being cultured according to the above procedure. As can be seen from FIG. 42, the expanded circulating tumor cells 21 express the fluorescence signals of Pan-CK, epithelial cell adhesion molecule (EpCAM) and DPAI (4',6-diamidino-2-phenylindole), but not the fluorescence signal of CD45. FIGS. 43 and 44 show the growth states of the pancreatic cancer-derived circulating tumor cells 21 at day 25 after being cultured according to the above procedure. As can be seen from FIG. 44, the expanded circulating tumor cells 21 express the fluorescence signals of Pan-CK, EpCAM, and DPAI, but not the fluorescence signal of CD45. FIGS. 45 and 46 show the growth states of the small cell lung cancer-derived circulating tumor cells 21 at day 39 after being cultured according to the above procedure. As can be seen from FIG. 46, the expanded circulating tumor cells 21 express the fluorescence signals of synaptophysin, thyroid transcription factor-1 (TTF-1) and DPAI, but not the fluorescence signal of CD45.

As can be known from above figures, the circulating tumor cells 21 derived from breast cancer, pancreatic cancer, and small cell lung cancer can form many cell colonies on the multi-particle colloidal crystal layer 12, the growth state is good, and the amplification speed is fast.

Figure 47:
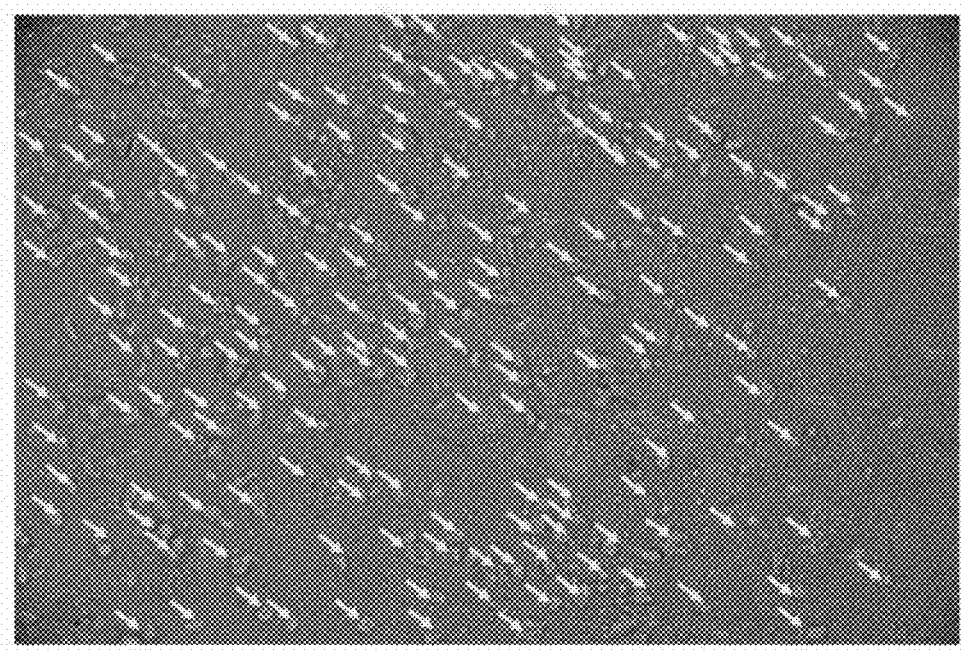
FIG. 47 is a micrograph showing the amplification state of the breast cancer-derived circulating tumor cells on the surface of the multi-particle colloidal crystal layer as shown in FIG. 25A and FIG. 25B.
Figure 48:
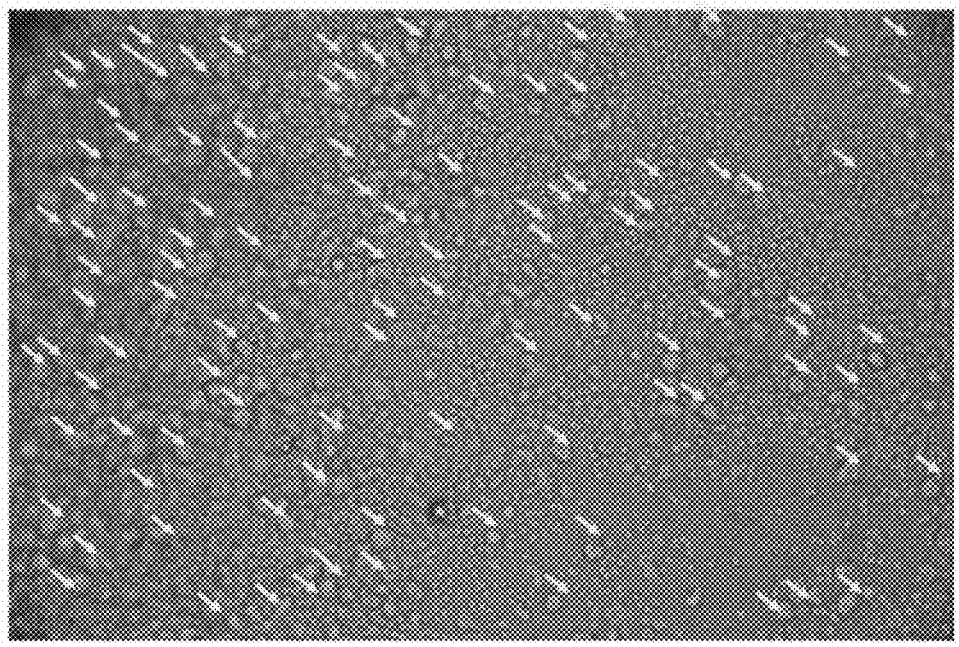
FIG. 48 is a micrograph showing the amplification state of the breast cancer-derived circulating tumor cells on the surface of the multi-particle colloidal crystal layer as shown in FIG. 24A and FIG. 24B.
Figure 49:
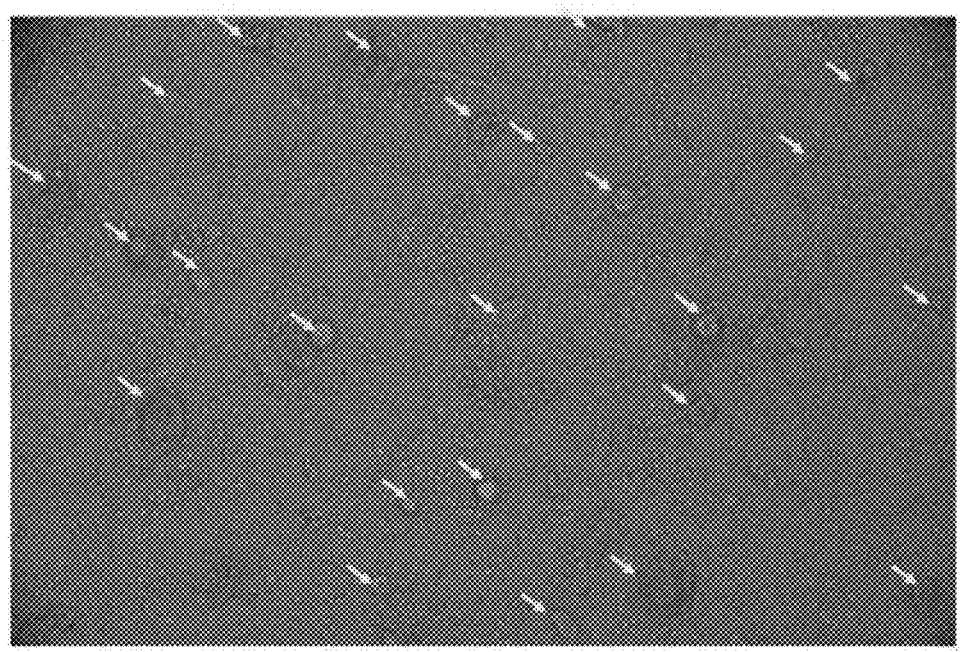
FIG. 49 is a micrograph showing the amplification state of the breast cancer-derived circulating tumor cells on the surface of the multi-particle colloidal crystal layer as shown in FIG. 23A and FIG. 23B.
Figure 50:
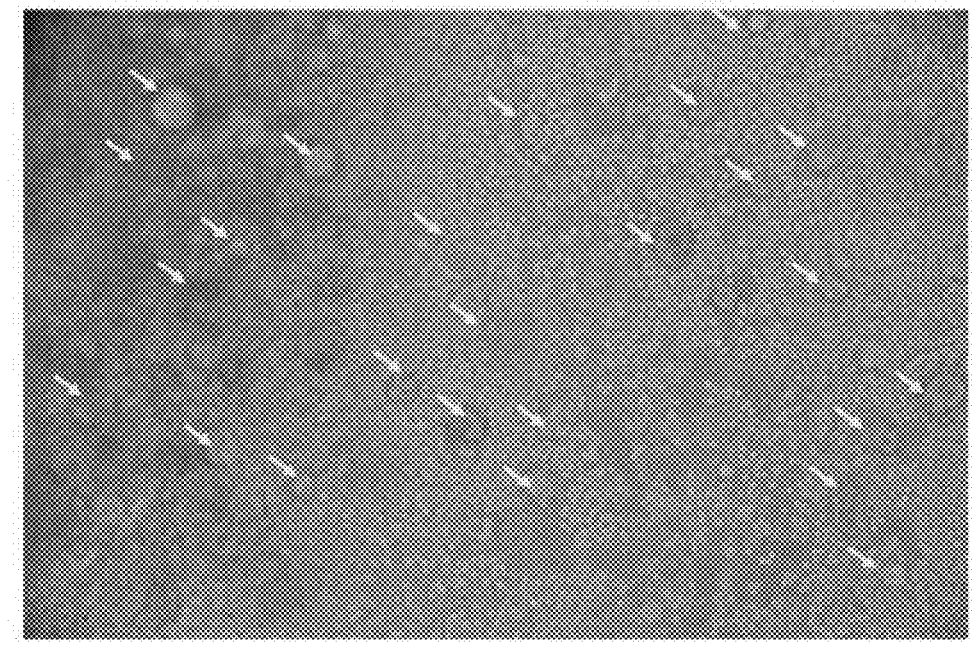
FIG. 50 is a micrograph showing the amplification state of the breast cancer-derived circulating tumor cells on the surface of the multi-particle colloidal crystal layer as shown in FIG. 26A and FIG. 26B.
Figure 51:
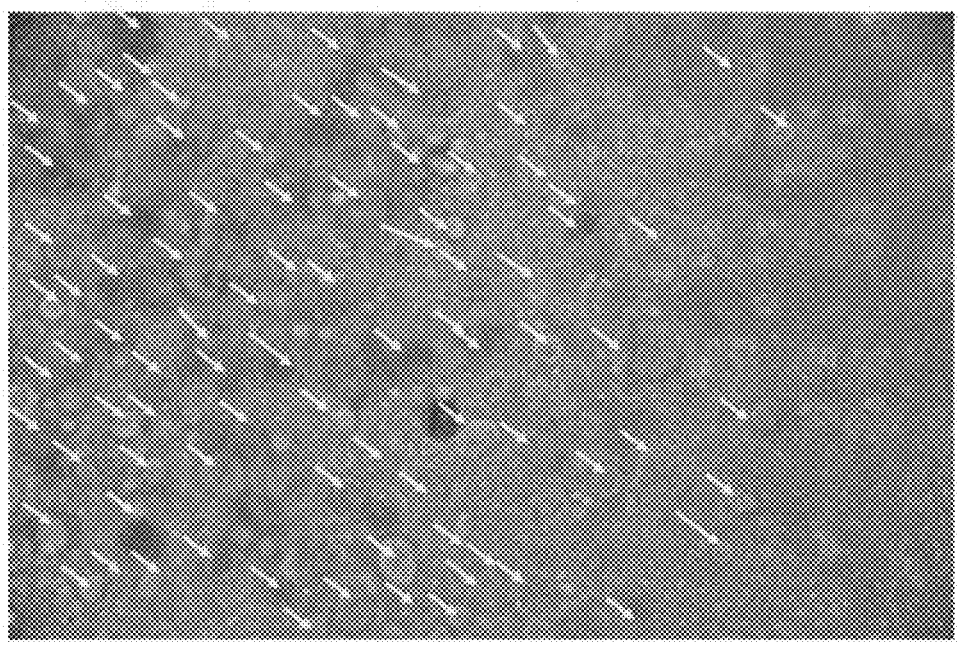
FIG. 51 is a micrograph showing the amplification state of the breast cancer-derived circulating tumor cells on the surface of the multi-particle colloidal crystal layer as shown in FIG. 9A and FIG. 9B.
Figure 52:
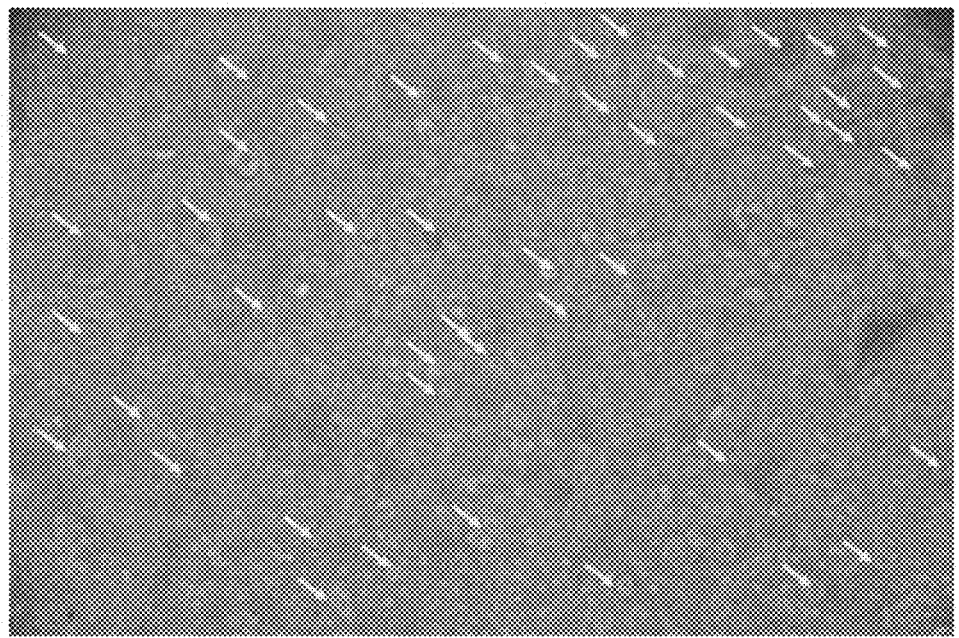
FIG. 52 is a micrograph showing the amplification state of the breast cancer-derived circulating tumor cells on the surface of the multi-particle colloidal crystal layer as shown in FIG. 10A and FIG. 10B.

FIGS. 47 to 52 show the amplification states of the breast cancer-derived circulating tumor cells on various cell culture tools 10. The amplification state of the breast cancer-derived circulating tumor cells 21 on the cell culture tool 10 with a multi-particle colloidal crystal layer 12 having Si particles having a particle size of 5000 nm and PS particles having a particle size of 400 nm is as shown in FIG. 47, indicating that the multi-particle colloidal crystal layer 12 obviously has many colonies formed through expanding the circulating tumor cells 21 thereon (indicated by the arrows). The amplification state of the breast cancer-derived circulating tumor cells 21 on the cell culture tool 10 with a multi-particle colloidal crystal layer 12 having Si particles having a particle size of 5000 nm and PS particles having a particle size of 200 nm is as shown in FIG. 48, indicating that the multi-particle colloidal crystal layer 12 obviously has many colonies formed through expanding the circulating tumor cells 21 thereon (indicated by the arrows). The amplification state of the breast cancer-derived circulating tumor cells 21 on the cell culture tool 10 with a multi-particle colloidal crystal layer 12 having Si particles having a particle size of 5000 nm and PS particles having a particle size of 65 nm is as shown in FIG. 49, indicating that the multi-particle colloidal crystal layer 12 obviously has many colonies formed through expanding the circulating tumor cells 21 thereon (indicated by the arrows). The amplification state of the breast cancer-derived circulating tumor cells 21 on the cell culture tool 10 with a multi-particle colloidal crystal layer 12 having Si particles having a particle size of 5000 nm and PSC particles having a particle size of 100 nm is as shown in FIG. 50, indicating that the multi-particle colloidal crystal layer 12 obviously has many colonies formed through expanding the circulating tumor cells 21 thereon (indicated by the arrows). The amplification state of the breast cancer-derived circulating tumor cells 21 on the cell culture tool 10 with a multi-particle colloidal crystal layer 12 having Si particles having a particle size of 2000 nm and PS particles having a particle size of 65 nm is as shown in FIG. 51, indicating that the multi-particle colloidal crystal layer 12 obviously has many colonies formed through expanding the circulating tumor cells 21 thereon (indicated by the arrows). The amplification state of the breast cancer-derived circulating tumor cells 21 on the cell culture tool 10 with a multi-particle colloidal crystal layer 12 having Si particles having a particle size of 2000 nm and PSC particles having a particle size of 100 nm is as shown in FIG. 52. As can be known from above figures, the circulating tumor cells 21 grow vigorously and form more and larger colonies on the cell culture tool 10 with a multi-particle colloidal crystal layer having various combinations of particles.

Figure 53:
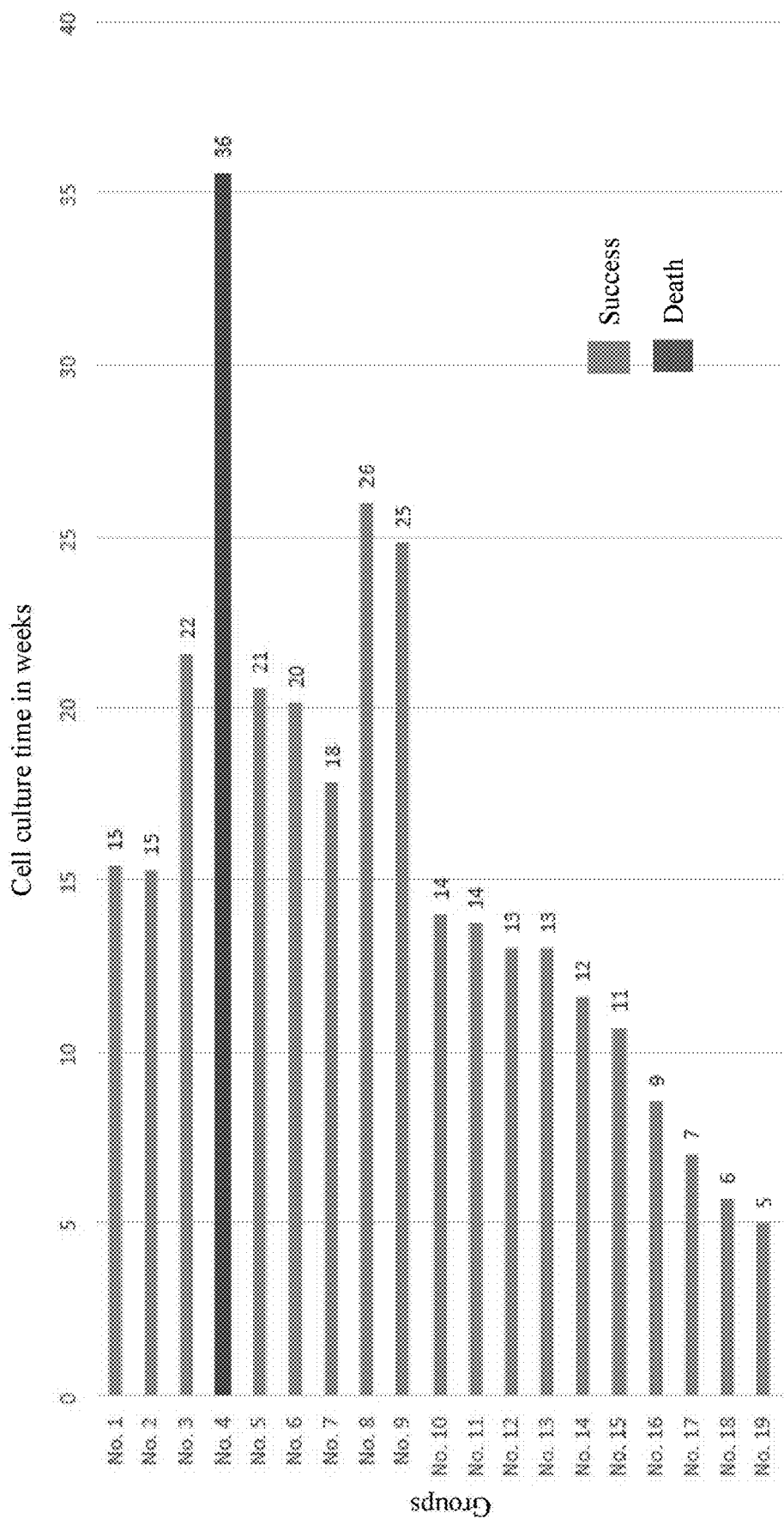
FIG. 53 shows the relationship between the amplification time in weeks and the living states of 19 groups of circulating tumor cells.

FIG. 53 shows the amplification time in weeks and the living states of 19 groups of circulating tumor cells 21. The cells are expanded following the method for expanding circulating tumor cells in vitro. The group where the cells are expanded by more than 20 times and grow continuously after 5 weeks of amplification is considered as a successful case, and the group where cells are dead after five weeks of amplification is considered as a failure case. As can be seen from FIG. 53, 18 out of the 19 cases in this experiment have more than 20-time expanding CTCs and the cells can grow continuously. That is, the success rate of expanding the circulating tumor cells 21 by the method for in-vitro expanding circulating tumor cells can reach 95% (18/19*100%).

According to the above procedure, the circulating tumor cells 21 are isolated from the blood of two patients with small cell lung cancer and cultured. Then cisplatin, etoposide and Topotecan injection are fed to the cell solution 20. The cell viability was measured by CellTiter Luminescent cell viability and the survival rate is calculated by the following formula:

Cell survival rate(%)=(luminescence density in the treated group/luminescence density in the control group)×100%.

Figure 54:
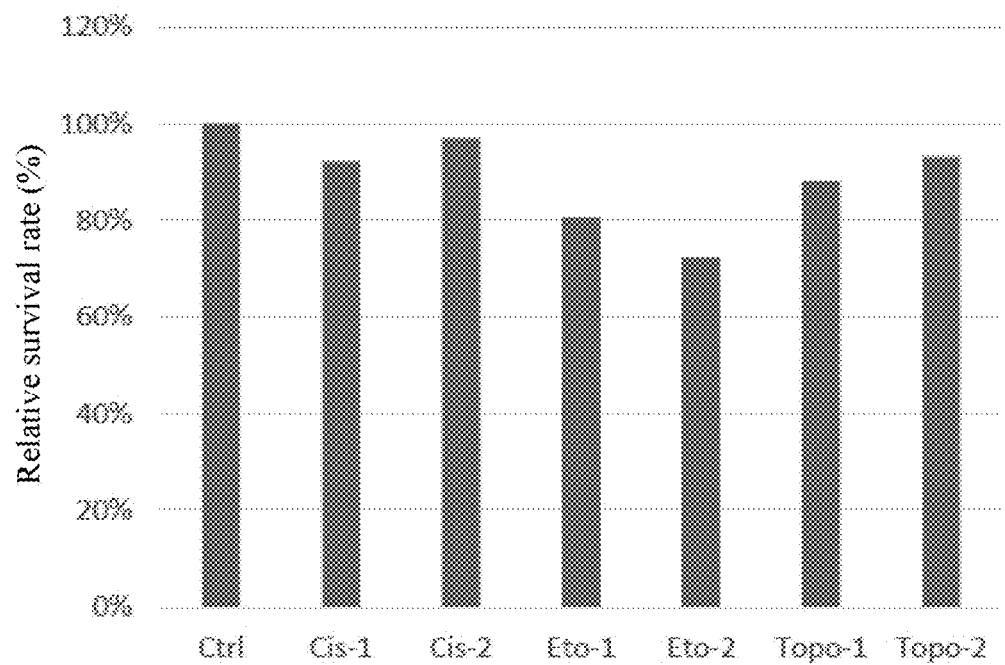
FIG. 54 shows the changes in the viability of the circulating tumor cells derived from one of two patients with small cell lung cancer in response to cisplatin, etoposide, and Topotecan.
Figure 55:
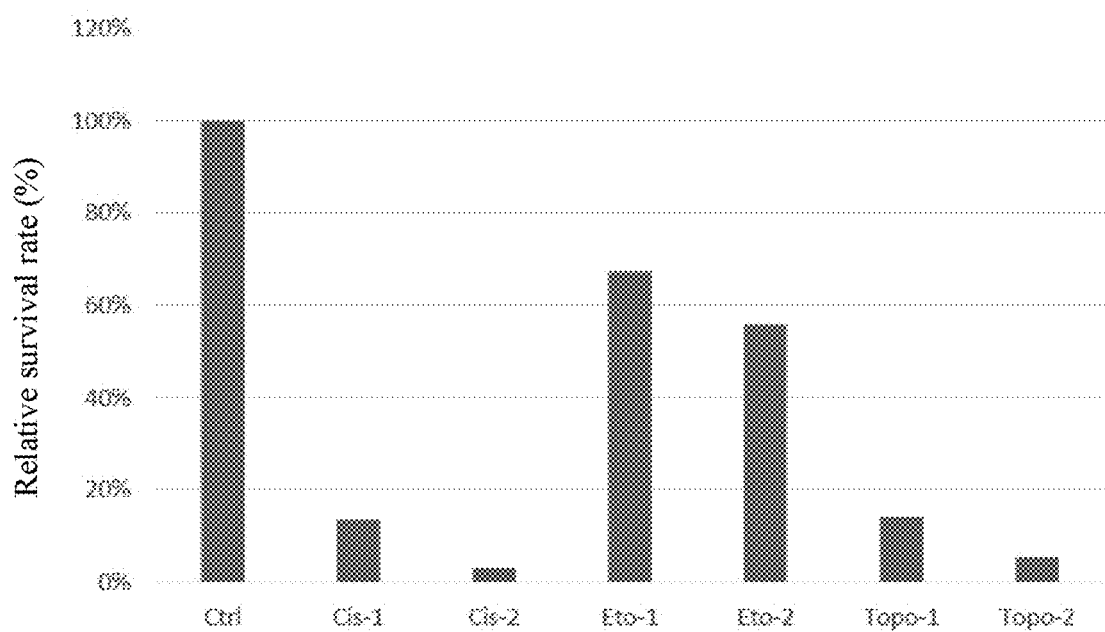
FIG. 55 shows the changes in the viability of the circulating tumor cells derived from the other of two patients with small cell lung cancer in response to cisplatin, etoposide, and Topotecan.

FIGS. 54 and 55 show the changes in the viability of the circulating tumor cells 21 derived from these two patients with small cell lung cancer in response to cisplatin, etoposide, and Topotecan, respectively. The treatment groups Cis-1 and Cis-2 represent groups administered with different amounts of cisplatin, the treatment groups Eto-1 and Eto-2 represent groups administered with different amounts of etoposide, the treatment groups Topo-1 and Topo-2 represent groups administered with different amounts of Topotecan, and Ctrl represents the control group.

As can be known from FIG. 54, in the presence of cisplatin, etoposide, and Topotecan, the survival rate of the circulating tumor cells 21 derived the blood of the first patient is more than 85%, and there is no significant decrease compared with the control group Ctrl. In other words, the test results show that the three agent cisplatin, etoposide, and Topotecan cannot inhibit the activity of the circulating tumor cells 21 derived from the blood of the patients with small cell lung cancer. In combination with the outcome where the patient is treated with cisplatin, etoposide, and Topotecan clinically, it can be further confirmed that these three drugs have no significant therapeutic effect on the small cell lung cancer in the patients.

As can be known from FIG. 55, in the presence of cisplatin and topotecan, the survival rate of the expanded circulating tumor cells 21 from the second patient is less than 20%, and there is significant decrease compared with the control group Ctrl. Moreover, in the presence of etoposide, the survival rate of the expanded circulating tumor cells 21 from the second patient is also lower than the control group Ctrl. In combination with the outcome where the patient is treated with cisplatin, etoposide, and Topotecan clinically, it can be further confirmed that the cisplatin and topotecan respond well to small cell lung cancer in the second patients, that is, have therapeutic effect.

It can be seen that by adding the drugs into the cell solution 20 and detecting the changes in cell activity, results that are consistent with the outcome obtained in clinical application are obtained, and drugs that are more suitable for individual patients can be evaluated and screened more accurately.

In summary, in the method and kit for expanding circulating tumor cells in vitro according to the embodiments of the present invention, a cell culture tool 10 with a multi-particle colloidal crystal layer having a suitable range of particle sizes on the surface are employed to enable the circulating tumor cells 21 attach to it and expand effectively. Moreover, the method and kit for expanding circulating tumor cells in vitro according to the embodiments of the present invention allow the circulating tumor cells 21 to be rapidly expanded by 20 times or more in 6 weeks or less. Furthermore, in the method and kit for expanding circulating tumor cells in vitro according to the embodiments of the present invention, after the amplification, the expanded circulating tumor cells 21 are further applicable to the evaluation of drugs, so as to rapidly screen related drugs for treating corresponding cancers.

What is claimed is:
1. A method for expanding circulating tumor cells in vitro, comprising:
   preparing a cell culture tool comprising:
      a two-dimensional planar surface; and
      a multi-particle colloidal crystal layer, located on the two-dimensional planar surface, and comprising a plurality of first particles having a particle size of 1000 to 5000 nm and a plurality of second particles having a particle size of 20 to 400 nm;
   preparing a cell solution, comprising a culture medium and a plurality of circulating tumor cells, wherein the culture medium comprises a platelet lysate; and contacting the cell solution with the multi-particle colloidal crystal layer, to attach the circulating tumor cells to the multi-particle colloidal crystal layer and expand to a given condition.

2. The method for expanding circulating tumor cells in vitro according to claim 1, wherein the first and second particles are made from any two of silicon, polystyrene, carboxylated polystyrene, poly(methyl methacrylate), gelatin, polycaprolactone, and poly (lactic-co-glycolic acid).

3. The method for expanding circulating tumor cells in vitro according to claim 1, wherein the step of preparing the cell culture tool comprises:
   mixing the first particles, the second particles and a solvent to form a colloidal solution;
   coating the colloidal solution on the two-dimensional planar surface;
   drying the colloidal solution on the two-dimensional planar surface, to dry the colloidal solution into the multi-particle colloidal crystal layer; and
   immobilizing the multi-particle colloidal crystal layer onto the two-dimensional planar surface.

4. The method for expanding circulating tumor cells in vitro according to claim 1, wherein the concentration of the platelet lysate is 3-20% of the culture medium.

5. The method for expanding circulating tumor cells in vitro according to claim 1, wherein the multi-particle colloidal crystal layer further comprises a plurality of third particles, wherein third particles have a particle size different from that of the first particles, and are made from a material different from that of the second particles.

6. The method for expanding circulating tumor cells in vitro according to claim 1, further comprising:
   adding a drug candidate to the cell solution containing the expanded circulating tumor cells;
   detecting the survival rate of the circulating tumor cells in the cell solution; and
   determining whether the drug candidate reduces the survival rate of the circulating tumor cells or not.

7. The method for expanding circulating tumor cells in vitro according to claim 6, wherein the circulating tumor cells are tumor cells derived from small cell lung cancer, lung cancer, breast cancer, pancreatic cancer, sarcoma, melanoma, liver cancer, esophagus cancer, colorectal cancer, or nasopharyngeal carcinoma.

8. A kit for expanding circulating tumor cells in vitro, comprising
   culture medium materials, for formulating a culture medium comprising a platelet lysate; and
   a cell culture tool, for accommodating the culture medium, wherein the cell culture tool comprises
   a two-dimensional planar surface; and
   a multi-particle colloidal crystal layer, located on the two-dimensional planar surface, and comprising a plurality of first particles having a particle size of 1000 to 5000 nm and a plurality of second particles having a particle size of 20 to 400 nm.

9. The kit for expanding circulating tumor cells in vitro according to claim 8, wherein the first and second particles are made from at least one of silicon, polystyrene, carboxylated polystyrene, poly(methyl methacrylate), gelatin, polycaprolactone, and poly (lactic-co-glycolic acid).

10. The kit for expanding circulating tumor cells in vitro according to claim 8, wherein the concentration of the platelet lysate is 3-20% of the culture medium.

* * * * *